(12) United States Patent
Dove et al.

(10) Patent No.: US 7,897,834 B2
(45) Date of Patent: Mar. 1, 2011

(54) MUTATION IN THE RAT ADENOMATOUS POLYPOSIS COLI GENE WITHIN THE HUMAN MUTATION HOTSPOT REGION

(75) Inventors: William F. Dove, Madison, WI (US); Michael N. Gould, Madison, WI (US); Lawrence N. Kwong, Madison, WI (US); James M. Amos-Landgraf, Madison, WI (US); Jill D. Haag, Mt. Horeb, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 194 days.

(21) Appl. No.: 11/591,653

(22) Filed: Nov. 1, 2006

(65) Prior Publication Data

US 2007/0143867 A1 Jun. 21, 2007

Related U.S. Application Data

(60) Provisional application No. 60/732,732, filed on Nov. 1, 2005.

(51) Int. Cl.
*A01K 67/00* (2006.01)
*C07H 21/04* (2006.01)

(52) U.S. Cl. ............... 800/10; 800/3; 800/8; 800/9; 536/23.1

(58) Field of Classification Search .................. None
See application file for complete search history.

(56) References Cited

U.S. PATENT DOCUMENTS 5,994,075 A 11/1999 Goodfellow et al.

OTHER PUBLICATIONS

Filippo et al. Brit J Cancer 1998;77:2148-51.*
Burnouf et al. Carcinogen 2001;22:329-35.*
Kawamori et al. Carcinogen 2004;25:1967-72.*
SEQ ID No. 16-Kakiuchi document, Sequence database, 2010.*
Kakiuchi et al. PNAS 1995;92:910-4.*
SEQ ID No. 16-Kakiuchi-NA document, Sequence database, 2010.*
2003/0150001 Gould, Aug. 7, 2003.
Altschul et al., 1997, *Nucl. Acids Res* 25: 3389-3402.
Ausubel, *Current Protocols in Molecular Biology* vol. 1-3, John Wiley & Sons, Inc.
Bickel and Docksum 2001, *Mathematical Statistics* vol. I, 2nd edition, Prentice-Hall, NJ.
Bulow, 2004, *Gut* 53: 381-386.
Chen and Gould, 2004, *Biotechniques* 37: 383-388.
Corpet and Pierre, 2005, *Eur. J. Cancer* 41: 1911-1922.
Dieffenbach et al., 1995, *PCR Primer: A Laboratory Manual*, Cold Spring Harbor Laboratory Press.
Haigis and Dove, 2003, *Nat. Genet.* 33: 33-39.
Karlin and Altschul, 1990, *Proc. Natl. Acad. Sci. USA* 87: 2267-2268.
Kriegler, 1990, *Gene Transfer and Expression: A Laboratory Manual*. Stockton Press, New York.
Moser et al., 1993, *Proc. Natl. Acad. Sci. USA* 90: 8977-8981.
Nakagama et al., 2005, *Cancer Sci.* 96: 627-636.
Pearson and Lipman 1988, *Proc. Natl. Acad. Sci. USA* 85: 2444-2448.
Sambrook et al., 2000, *Molecular Cloning: A Laboratory Manual*, 3rd ed., Cold Spring Harbor Laboratory Press.
Shoemaker et al., 1998, *Proc. Natl. Acad. Sci. USA* 95: 10826-10831.
Smith and Waterman, 1981, *Adv. Appl. Math.* 2: 482-489.
Smits and Cuppen, 2006, *Trends Genet.* 22: 232-240.
Smits et al., *Genomics* 83: 332-334.
Zan et al., *Nat Biotechnol.* 21:645-651.

* cited by examiner

*Primary Examiner*—Q. Janice Li
(74) *Attorney, Agent, or Firm*—Quarles & Brady LLP

(57) ABSTRACT

A rat with a disrupted Apc (adenomatous polyposis coli) gene is provided. The mutation can include an A to T transversion changing a lysine to a stop codon at codon 1137. Methods of generating the knockout rat are provided. Also provided is the offspring or progeny of that rat. In addition, methods of using these rats are provided, including methods for screening a carcinogen or a promoter of carcinogenesis, and methods for screening preventive and inhibitory agents of carcinogenesis.

8 Claims, 8 Drawing Sheets

FIGURE 3

```
              1         10        20        30        40        51
              |---------+---------+---------+---------+---------+|
    Human     RVGSNHGINQNVSQSLCQEDDYEDDKPTNYSERYSEEEQHEEEE-RPTNYS
      Dog     ............N........................-......
      Cow     ........S...N.......................G........-......
      Rat     .M..S.AV....N........................-......
    Mouse     .M..S.A.....N.................................E......
  Opossum     ..S.G.....K.N....H....DE.....................D-......
Zebrafish     SS..S..L.KKI..TI.SV...A.................L..QT---PS..
                                     ↑  ↑
                                     K→X Mutation
                                        15 aa
```

Pirc spleen *vs.* wild type spleen

Pirc spleen *vs.* Tumor 1

Pirc spleen *vs.* Tumor 2

MUTATION IN THE RAT ADENOMATOUS POLYPOSIS COLI GENE WITHIN THE HUMAN MUTATION HOTSPOT REGION

CROSS-REFERENCE TO RELATED APPLICATIONS

This invention claims priority to U.S. Provisional Patent Application Ser. No. 60/732,732 filed Nov. 1, 2005.

GOVERNMENT INTERESTS

This invention was made with United States government support under grant No. CA 063677 awarded by the NIH. The United States may have certain rights in this invention.

FIELD OF THE INVENTION

This invention is related to tumor-susceptible non-human animals and to the use of such animals in identification of anti-tumor agents.

BACKGROUND OF THE INVENTION

Familial adenomatous polyposis (FAP) is an inherited condition in which numerous polyps form mainly in the epithelium of the large intestine. While these polyps start out benign, malignant transformation into colon cancer occurs when the polyps are not treated. FAP can occur due to mutations in the Adenomatous Polyposis Coli (Apc) gene. The product of the Apc gene is a 300 kDa cytoplasmic protein associated with the adherence junction protein catenin. Humans with mutations in the Apc gene get hundreds to thousands of adenomas in the colon and typically develop colorectal cancer.

Experimental analysis of human colon cancer aims to develop an accurate model for studying tumor initiation, progression, and potential treatments. Much of modern cancer research is predicated on the establishment of animal tumor models, in particular rodent models. Murine (mouse) models are widely used. Traditionally, the rat has been favored for physiological studies while the mouse has been preferred for genetics.

One of the most widely distributed mouse models for studying human intestinal cancer is the $Apc^{Min}$ (Min) mouse, with a two month growth period for macroscopically visible, countable tumors. The $Apc^{Min}$ mouse was obtained through the use of chemical mutagenesis using N-ethyl-N-nitrosourea (ENU), and was described by Moser et al., 1993, *Proc. Natl. Acad. Sci. USA* 90: 8977-8981. The $Apc^{Min}$ mutant mice carry a single nonsense mutation in the adenomatosis polyposis coli (Apc) gene that results in a multiple intestinal neoplasia (Min) phenotype in affected mice—hence the name $Apc^{Min}$.

While the Apc gene is typically altered in humans similarly affected by colorectal tumors, there are important differences between the manifestations of the disease in humans and mice. The Min mouse and related mouse models including $Apc^{1638N/+}$ and $Apc^{\Delta 716}$ are not without their disadvantages. One of the main criticisms of the models is that the tumors arise primarily in the small intestine, in contrast to the colonic localization in human FAP patients. Mice are rarely used as models in major animal drug trials owing to their small size, short life span, and low amounts of recoverable plasma. Additionally, Min mice do not develop metastases to distant sites. Finally, mouse chromosomes are acrocentric, yet the analysis of mechanisms of loss of heterozygosity requires data on both arms of a metacentric chromosome. Although the Rb(7.18) 9Lub metacentric fusion line of mice provides a means to confirm somatic recombination in the Min mouse (Haigis and Dove, 2003, *Nat. Genet.* 33: 33-39), this translocation does not reflect the natural state, and the mice have a low colonic tumor incidence and multiplicity (21% incidence, <0.4 tumors per mouse). These differences are sufficiently significant to have prompted many researchers to use an alternative model, namely rats fed the colon carcinogen azoxymethane (AOM), to more closely mimic the etiology of the disease in humans.

The laboratory rat presents several advantages over the mouse: an increased size and longevity, an increased tolerance of tumor burden, and an overwhelming use for large-scale chemoprevention studies. Most important, the metacentric structure of rat chromosome 18 provides new ways to study the mechanisms of Apc loss of heterozygosity (LOH) that cannot be studied endogenously in the mouse and that cannot be manipulated in the human. The importance of the rat centers around a debate on the role of genomic instability in colon cancer, and whether genomic instability is necessary for tumor initiation, or genomic instability is acquired afterwards and either stimulates neoplastic progression or simply accumulates as the neoplasm advances. The rat could thus provide a metacentric model on which to test these hypotheses. However, at present, no embryonic stem cell lines exist for the rat, precluding knockout technology via traditional homologous recombination.

It would be advantageous to create a new animal model system for mimicking disease progression, prevention, and treatment for evaluation of human therapeutics in human intestinal cancer, including colorectal cancer. Such model system could be used for screening compounds for carcinogenic activity, as well as screening compound for carcinogenesis inhibitory activity. The present invention addresses these and other related needs.

SUMMARY OF THE INVENTION

This invention provides a mutant rat having a disruption in its Apc gene that prevents expression of a functional Apc protein, which results in increased susceptibility to tumor development in the rat's colon compared to a wild-type rat. The disruption in the Apc gene may result in tumor development in the rat's colon compared to a wild-type rat.

This invention provides a mutant rat having a disrupted Apc gene having the nucleotide sequence of Rat Genome Database ID No. 1554322 (SEQ ID NO:16).

The disruption in the Apc gene may result in a truncated Apc protein. The endogenous Apc gene may be disrupted by mutagenesis. The mutant rat may be an inbred line. The mutant rat may be heterozygous for the disruption in the Apc gene.

The disruption of the Apc gene in the mutant rat may be a germline mutation. The germline mutation may be passed to a somatic cell.

This invention provides the offspring or progeny of a mutant rat where the offspring or progeny has inherited the disrupted portion of the Apc gene. The offspring or progeny may include a disrupted Apc gene that has the nucleotide sequence of Rat Genome Database ID No. 1554322 (SEQ ID NO:16).

This invention provides a method for screening a compound for carcinogenic activity, which includes administering the compound to a mutant rat having a disruption in its Apc gene and comparing the incidence of tumors between the mutant rat administered with the compound and a mutant rat not administered with the compound. The disrupted Apc gene may have the nucleotide sequence of Rat Genome Database ID No. 1554322 (SEQ ID NO:16). The higher incidence of tumors may be indicative of the compound having carcinogenic activity and the lower incidence of tumors may be indicative of the compound not having carcinogenic activity. The method may include administering a compound having carcinogenesis inhibitory activity to the mutant rat.

This invention provides a method for screening a compound for carcinogenesis inhibitory activity, which includes administering the compound to a mutant rat having a disruption in its Apc gene and comparing the incidence of tumors between the mutant rat administered with the compound and a mutant rat having a tumor but not administered with the compound. The disrupted Apc gene may have the nucleotide sequence of Rat Genome Database ID No.1554322 (SEQ ID NO:16). Lower incidence of tumors may be indicative of the carcinogenesis inhibitory activity and a higher incidence of tumors may be indicative of the compound not having carcinogenesis inhibitory activity. The method may include administering to the mutant rat a compound having carcinogenic activity. Alternatively, the method may include administering to the mutant rat a compound suspected of having carcinogenic activity. The compound may be administered before tumor development. Alternatively, the compound may be administered after tumor development.

This invention provides a method of generating a mutant rat, which includes disrupting the rat's Apc gene, where the disruption prevents expression of the Apc gene and results in tumor development in the rat's colon. The disruption may include an A to T mutation in the Apc gene changing a lysine to a stop codon at codon position 1137. The disruption may be effected by mutagenesis. The mutagenesis may be chemical mutagenesis. The chemical mutagenesis may be effected using N-ethyl-N-nitrosourea. Alternatively, the mutagenesis may include mutagenesis using a transgenic construct. The transgenic construct may include the nucleotide sequence deposited under ID 1554322 in the Rat Genome Database.

This invention provides an isolated nucleic acid comprising the nucleotide sequence of Rat Genome Database ID No. 1554322 (SEQ ID NO:16). The invention provides a vector that includes the isolated nucleic acid sequence SEQ ID NO:16. The invention also provides a rat embryo that includes the isolated nucleic acid sequence SEQ ID NO:16.

BRIEF DESCRIPTION OF THE DRAWINGS

FIG. 3 illustrates a cross-species alignment of 50 amino acids surrounding the Pirc mutation. The alignment includes human (SEQ ID NO: 17), dog (SEQ ID NO: 18), cow (SEQ ID NO: 19), rat (SEQ ID NO: 20), mouse (SEQ ID NO: 21), opossum (SEQ ID NO: 22), and zebrafish (SEQ ID NO: 23) sequences.

DETAILED DESCRIPTION OF THE INVENTION

Figure 1:
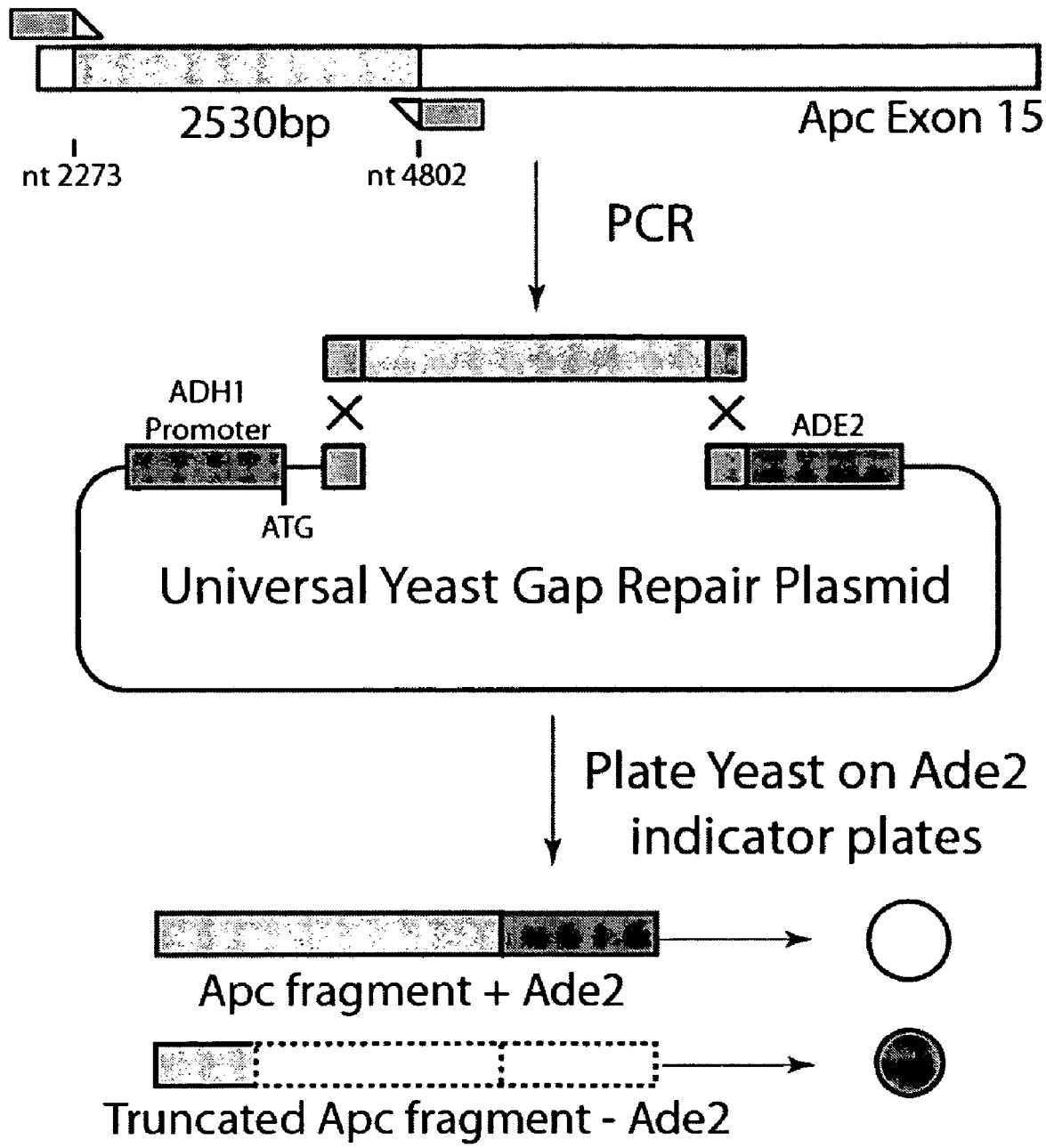
FIG. 1 depicts a schematic of the yeast-based screening protocol that was used for screening of DNA mutations in the ENU-mutagenized rats.

The practice of the present invention employs, unless otherwise indicated, conventional techniques of molecular biology (including recombinant techniques), microbiology, cell biology, biochemistry, immunology, protein kinetics, mass spectroscopy, and microscopy, which are within the skill of art. Such techniques are explained fully in the literature, e.g. in Sambrook et al., 2000, *Molecular Cloning: A Laboratory Manual*, 3rd ed., Cold Spring Harbor Laboratory Press; *Current Protocols in Molecular Biology* Volumes 1-3, John Wiley & Sons, Inc.; Kriegler, 1990, *Gene Transfer and Expression: A Laboratory Manual*. Stockton Press, New York; Dieffenbach et al., 1995, *PCR Primer: A Laboratory Manual*, Cold Spring Harbor Laboratory Press, each of which is incorporated herein by reference in its entirety.

Generally, the nomenclature and the laboratory procedures in recombinant DNA technology described below are those well known and commonly employed in the art. Standard techniques are used for cloning, DNA and RNA isolation, amplification and purification. Generally, enzymatic reactions involving DNA ligase, DNA polymerase, restriction endonucleases and the like are performed according to the manufacturer's specifications. Procedures employing commercially available assay kits and reagents are typically used according to manufacturer-defined protocols unless otherwise noted.

The terms "a", "an", "the" and the like, unless otherwise indicated, include plural forms.

The term "nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read-through by a polymerase and do not alter expression of a polypeptide encoded by that nucleic acid.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

The term "coding sequence" or "coding region" refers to a nucleic acid molecule having sequence information necessary to produce a gene product, when the sequence is expressed.

The term "genomic sequence" or "genome" refers to the complete DNA sequence of an organism.

The term "nucleic acid construct" or "DNA construct" is sometimes used to refer to a coding sequence or sequences operably linked to appropriate regulatory sequences so as to enable expression of the coding sequence, and inserted into a expression cassette for transforming a cell. This term may be used interchangeably with the term "transforming DNA" or "transgene". Such a nucleic acid construct may contain a coding sequence for a gene product of interest, along with a selectable marker gene and/or a reporter gene.

The term "label" refers to a composition detectable by spectroscopic, photochemical, biochemical, immunochemical, or chemical means. For example, useful labels include $^{32}$P, fluorescent dyes, colorimetric labels, electron-dense reagents, enzymes (e.g., as commonly used in an ELISA), biotin, digoxigenin, or quantum dots. As used herein, the term "label" also includes indirect labeling of proteins using detectable labels bound to other molecules or complexes of molecules that bind to a protein of interest, including antibodies and proteins to which antisera or monoclonal antibodies specifically bind. As used herein, the term "calorimetric label" includes a label that is detected using an enzyme-linked assay.

The phrases "disruption of the gene" and "gene disruption" refer to a mutation of the native, endogenous DNA sequence (usually one or more exons) and/or the promoter region of a gene so as to decrease or prevent expression of that gene in the cell as compared to the wild-type or naturally occurring sequence of the gene. Disruption of the Apc gene refers to a mutation of the Apc gene so as to decrease or prevent expression of the Apc gene. A mutant rat with a disrupted Apc gene is a rat that no longer expresses the Apc gene, or expresses the Apc gene at a decreased level as compared to the wild-type or naturally occurring sequence of the Apc gene.

The term "knockout" or "gene knockout" refers to partial or complete suppression of the expression of at least a portion of a protein encoded by an endogenous DNA sequence in a cell. The term "knockout rat" refers to a genetically engineered rat one or more of whose genes have been made inoperable through a gene knockout.

A "transgenic construct" is a recombinant construct that includes the disrupted Apc nucleotide sequence. For example, a "transgenic construct" may refer to a nucleic acid sequence that is designed to decrease or suppress expression of a protein encoded by endogenous DNA sequences in a cell. The nucleic acid sequence used as such transgenic construct is typically comprised of (1) DNA from some portion of the gene (exon sequence, intron sequence, and/or promoter sequence) to be suppressed and (2) a marker sequence used to detect the presence of the transgenic construct in the cell. The transgenic construct is inserted into a cell, and integrates with the genomic DNA so as to prevent or interrupt transcription of the native DNA sequence. Such insertion usually occurs by homologous recombination (i.e., regions of the transgenic construct that are homologous to endogenbus DNA sequences hybridize to each other when the transgenic construct is inserted into the cell and recombine so that the transgenic construct is incorporated into the corresponding position of the endogenous DNA). The transgenic construct nucleic acid sequence may include a full or partial sequence of one or more exons and/or introns of the gene to be suppressed, a full or partial promoter sequence of the gene to be suppressed, or combinations thereof. The transgenic construct can be inserted into a recombinant or expression vector. The transgenic construct can be inserted into an embryonic stem cell (ES cell) and is integrated into the ES cell genomic DNA, usually by the process of homologous recombination. This ES cell is then injected into, and integrates with, the developing embryo.

The terms "rodent" and "rodents" refer to all members of the phylogenetic order Rodentia including any and all progeny of all future generations derived therefrom.

The term "murine" refers to any and all members of the family Muridae, including rats and mice.

The term "isogenic" refers to an inbred line characterized by essentially identical genes.

The term "colon" refers to the part of the intestine that extends from the cecum to the rectum.

The terms "progeny" or "offspring" refer to any and all future generations derived and descending from a particular mammal, and in particular, to a rat containing a mutation in the Apc gene. Thus, progeny of any successive generation are included herein such that the progeny, the F1, F2, F3, generations and so on indefinitely are included in this definition.

The term "germline mutation" is any detectable, heritable variation in the lineage of germ cells. Mutations in these cells are transmitted to offspring.

The term "congenic" refers to organisms that genetically differ in one locus. For example, congenic rats are generated by mating two inbred rat strains, and backcrossing the descendants a number of generations with one of the strains, the recipient strain. Conversely, the strain that contributes the smallest amount of genetic material is termed the donor strain.

The term "carcinogen" refers to any substance or agent that promotes cancer.

A compound "having carcinogenesis inhibitory activity" refers to a compound that is capable of preventing carcinogenesis and/or inhibiting growth of tumors.

Optimal alignment of sequences for comparison may be conducted by methods commonly known in the art, e.g., the local homology algorithm (Smith and Waterman, 1981, *Adv. Appl. Math.* 2: 482-489), by the search for similarity method (Pearson and Lipman 1988, *Proc. Natl. Acad. Sci. USA* 85: 2444-2448), by computerized implementations of these algorithms (GAP, BESTFIT, BLAST, FASTA, and TFASTA in the Wisconsin Genetics Software Package, Genetics Computer Group (GCG), Madison, Wis.), or by inspection.

Protein and nucleic acid sequence identities are evaluated using the Basic Local Alignment Search Tool ("BLAST") which is well known in the art (Karlin and Altschul, 1990, *Proc. Natl. Acad. Sci. USA* 87: 2267-2268; Altschul et al., 1997, *Nucl. Acids Res.* 25: 3389-3402). The BLAST programs can be used with the default parameters or with modified parameters provided by the user.

The particular gene that is the subject of the present invention is Apc (Adenomatous Polyposis Coli), which is involved in familial colon cancer.

The present invention provides mutagenized rat that simulates or mimics human colon cancer, and can thus be used as a valuable model system for studying human colon cancer. This invention provides a Pirc rat (the terms "Pirc"—"Polyposis in the Rat Colon" or $Apc^{Pirc}$ are used interchangeably herein), a rat knockout model of human familial adenomatous polyposis. The Pirc rat has a disrupted Apc gene. Preferably, the Pirc rat has a single point mutation with an A to T transversion changing a lysine to a stop codon at codon 1137 in the polypeptide encoded by the Apc gene. Thus, functional Apc protein is not expressed in somatic cells of the mutant rat.

This invention provides the isolation of a truncating mutation of the Apc gene in rats. The mutation of the Apc gene in rats can be somatic or germline. Preferably, the truncating mutation of the Apc gene in rats is a germline mutation.

Knockout (i.e. loss-of-function or change-in-function) rats can be produced by methods known in the art, such as somatic ENU treatment described in the examples below and in Moser et al., 1993, *Proc. Natl. Acad. Sci. USA* 90: 8977-8981, ENU mutagenesis followed by the screening of genes of interest by direct sequencing (Smits et al., 2006, *Trends Genet.* 22: 232-240), or by a calorimetric yeast assay (Zan et al., 2003, *Nat. Biotechnol.* 21: 645-651). A broad screen-based method of chemically mutagenizing rodents to produce either germline or autologus mutations can be used to obtain knockout rats, as disclosed in U.S. Patent Application No. 2003/0150001. This method is unusual in that animals are administered mutagen (e.g., by feeding), rather than produced transgenically, and then screened for the presence of mutations in desired genes rather than selected by virtue of their phenotype. A method of identifying a mutation in a gene of interest is then used, such as the method disclosed in U.S. Pat. No. 5,994,075. For example, a founder of the Pirc rat kindred can be identified by screening genomic DNAs from the progeny of N-ethyl-N-nitrosourea (ENU) treated males for truncating mutations in Apc. The mutagenized males can be selected from an inbred line of rats, e.g. the inbred Fisher-344 line of rats. Screening can be performed using a yeast gap-repair, ADE2-reporter truncation assay. Rats can also be mutagenized using target-selected mutagenesis (Smits et al., 2004, *Genomics* 83: 332-334).

Preferably, about 2530 bases of Apc exon 15 are amplified with chimeric primers for the rat Apc sequence carrying homology to a "universal vector" that accepts any such chimeric amplicon. The amplicon is then gap-repaired into the universal vector and transformed into ADE2-deficient yeast. Screening of the F1 progeny is performed to yield a single plate with half red, half white colonies; this is the expected ratio for a heterozygous mutant. The mutation in this Pirc rat is then confirmed by sequencing. Preferably, the mutation is at nucleotide position 3409 of the Apc gene, creating a K to $X^{am}$ (AAG to TAG) change, thereby creating a stop codon at position 1137. This Pirc ($Apc^{Pirc}$) allele is registered in the Rat Genome Database (RGD) and RGD_ID 1554322 has been assigned to it. It is shown here as SEQ ID NO:16.

The present invention also provides the offspring or progeny of the Pirc rat. The mutation in the Pirc rat of this invention has been successfully transmitted to more than 60 offspring, and to 5 progeny generations.

The Pirc rat can be used for screening of carcinogens and promoters of carcinogenesis. Thus, the present invention provides a method for screening a compound for carcinogenic activity using the Pirc rat of this invention.

The Pirc rat can also be used for screening of compound for carcinogenesis inhibitory activity. Thus, the present invention provides a method for screening compound for carcinogenesis inhibitory activity, using the Pirc rat of this invention.

The screening of compounds for carcinogenesis activity and/or screening of compounds for carcinogenesis inhibitory activity can include longitudinal studies on a set of tumors within a rat, whose addresses are established by imaging (e.g. microCT, microPET) or endoscopy on the living rat. The endoscope permits to obtain pinch or snare biopsies from tumors. Sufficient DNA can be obtained from these biopsies to carry out Pyrosequencing using primers that flank the informative SNP sites in a heterozygote carrying the Pirc mutation. Tumor volume calculations can be done in Amira 4.1 (Mercury Computer Systems, Inc., Chelmsford, Mass.).

The inhibitory or the carcinogenic activity of compounds can be determined by the calculation of tumor multiplicity in experimental animals versus control untreated animals. Comparison between tumors at different stages can be performed. Furthermore, each rat provides in the range of 5 to 10 colonic tumors to study. If the tumors were independent across animals, this would reduce by a factor of 5 to 10 the number of animals needed. Independence will not be assumed, but even accounting for correlation within animals, the overall sample size required is reduced compared to a standard experimental design.

The analysis of tumor response on the basis of endoscopic, microCT, and microPET images can be validated by establishing the confidence limits of these measurements. The first step of validation is to measure the coefficient of variation in a series of replicate measurements on the same tumor by each modality. This coefficient of variation is expected to differ for different sizes of tumors, and perhaps for different biological classes. The microPET images can also vary with the batch of radiolabeled probe. Overall, no rigorous conclusion can stand if it is based upon differences that are not significantly different from the salient coefficient of variation of the measurement. A precaution that can routinely be taken in measurements that could involve observer bias is to score blind to the identity of the sample.

To the inventors' knowledge this is the first mutant rat to be generated on a completely inbred line. The Pirc rat can be used as a cancer "test" model for multiple purposes. In principle, it is possible to treat the Pirc rat with various carcinogens, agents for treatment and prevention of carcinogenesis, biomarkers, labels, modifiers, or to subject the Pirc rat to various types of surgery, in order to study colorectal tumor initiation, progression, and potential treatments. These studies could then be used as bases for treatments of humans that have developed colorectal cancer, or are susceptible to developing one. One skilled in the art will know to cross the Pirc rat with other rat strains, transgenic rats, and knockouts, to generate a cross of the Pirc mutation into other desirable genetic backgrounds. The resulting progeny can be used for a variety of assays related to colorectal tumor initiation, progression, and potential treatments. Therefore, the Pirc rat kindred will enhance our ability to study the development, progression, physiology and treatment of disease.

Some Advantages of the Pirc Rat Over Prior Models

Much of modern cancer research is predicated on the establishment of tractable and quantitative animal tumor models, in particular rodent models. (Nakagama et al., 2005, *Cancer Sci.* 96: 627-636). Some of the reasons for the value of the Pirc rat are highlighted in a recent article that provides a systematic review and meta-analysis of colon chemoprevention in rats, mice, and men, and discusses the suitability of rodent models of carcinogenesis in predicting efficacy in humans (Corpet and Pierre, 2005, *Eur. J. Cancer* 41: 1911-1922). Some of the advantages of the Pirc rat over prior models for colon chemoprevention are highlighted below. Pirc rats in accordance with this invention have one or more of these advantages.

Apc, the gene mutated in the Pirc rat, is the primary gene mutated in both sporadic and familial human colon tumors. Min, the analogous mouse model of colorectal cancer, the first mouse model of cancer that developed tumors that are easily observed, develops 0-4 colonic tumors, but has a short lifespan (3-6 months) owing to >40 small intestinal adenomas. In contrast, Pirc rats develop 3-6 colonic tumors with a long lifespan (>8 months) owing to <10 small intestinal adenomas, allowing for better assessment of tumor progression. In this respect at least, the Pirc rat is superior to the Min mouse. It is also the first knockout rat that develops such easily viewable tumors.

The Pirc rat is already on an inbred Fischer-344 background, which permits its study under genetically homogenous inbred conditions and a broad range of F344 $Apc^{Pirc/+}$ x (i.e., other inbred) conditions. The heterozygous mutation is transmissible in normal Mendelian ratios.

Table 1 compares human Apc-derived colorectal cancer, the $Apc^{Min}$ mouse, the AOM rat models (rat+carcinogen), and the rat model of this invention (Pirc rat). Ranges are for strain averages, not for individual animals. The founding mutation in ~-100% of human FAP and Min mouse intestinal tumors is in the Apc gene, but ~50% of carcinogen-induced rat tumors have the founding mutation in the beta-catenin gene. Chromosome status is important because it might affect the rate at which the Apc mutation undergoes loss of heterozygosity.

The majority of data for carcinogen-treated rats uses time points later than 10 months of age.

TABLE 1

Colorectal cancer phenotype comparisons

|  | Average colonic tumor count (age observed) | Average colonic tumor incidence | Average colonic:small intestinal tumor count ratio | Chromosomal organization |
|---|---|---|---|---|
| Human FAP (codon 700-1500) | >100 (>12 yrs) | 100% | >1:1 | Metacentric |
| C57BL/6J-Min Mouse (codon 850) | 2-4 (>4 mos) | 40-80% | <1:40 | Acrocentric |
| F344 rat treated with carcinogen (typically β-catenin mutations) | 1-2 (>10 mos) | 80-90% | 0:1 | Metacentric |
| F344-Pirc rat (codon 1137) | 10 (>4 mos) | 100% | 1:1 | Metacentric |

Current rat models of colon cancer induced by chemical carcinogens such as AOM, DMB, and PhiP have significant limitations: they require long-term (>8 months) time for development of tumors versus <6 months for the Pirc rat; they develop an average of less than one tumor per animal, versus an average of five tumors in the Pirc rat. The existence of more tumors per animal translates to fewer animals needed for statistical significance. Also, few of these chemically-induced tumors (<20%) develop from a mutation in the Apc gene, versus ~100% of tumors in the Pirc rat. The current rat models also require administration of carcinogens for all rats, whereas Pirc rats require no treatment for the development of tumors, decreasing costs and time investments. Finally, they have inconsistent results due to differences in administration and dose responses, again requiring more animals to create a statistically significant result, versus a tight distribution of tumor multiplicity in Pirc rats.

Existing rodent models for colorectal cancer do not fully recapitulate progression of the disease in humans. The rat model affords a much greater opportunity to understand disease progression and potentially efficacy of new treatments envisioned for humans. In short, the new Apc rat model more effectively mimics the genotypic and phenotypic human disease than either the Apc$^{Min}$ mouse or the AOM rat models. Shown in Table 2 are some of the phenotypic advantages that the Pirc rat provides in comparison to other known carcinogen-treated rats.

TABLE 2

Comparative advantages of known carcinogen-treated rats and the Pirc rat of the present invention

| Summary of differences (for the F344 strain) | Carcinogen treated rats | Pirc rat |
|---|---|---|
| Average number of tumors | <1 | ~5 |
| Time for experimental tumor development | >8 mos | <6 mos |
| Primary tumor mutation | beta-catenin | Apc |
| Treatment required for tumor formation? | Yes | No |
| Consistent tumor multiplicities? | No | Yes |

The Pirc rat of this invention does not have to have all of the above advantages over prior models for colon chemoprevention. The Pirc rat has at least one of the above advantages over prior models.

The following examples are offered to illustrate, but not to limit the claimed invention.

EXAMPLES

Rats. Rats were maintained in standard, non-microisolator cages. Rats were fed either 5020 chow (Purina, St. Louis, Mo.) or 8604 chow (Teklad, Madison, Wis.) with access to an automatic water supply. The following rat strains were used: F344/NTac; WF/NHsd; and SD/Hsd. The colons of 3 rats were perfused with PBS to stretch the muscularis into a flat sheet. The square area of each was measured with a ruler and used to normalize the square area of non-perfused colons to perfused ones. Tumors per square area were then calculated and averaged and the histology was assessed.

Colorimetric Yeast Assay. The N-Ethyl-N-Nitrosourea (ENU) treatment of male rats for the mutagenesis screen was performed as previously described (Zan et al., 2003, *Nat. Biotechnol.* 21: 645-651). F344 males were given an injection of 60 mg/kg of ENU once per week for two weeks.

Long-range PCR off of genomic DNA was performed using the following primers: Forward: GGC CAT CGA TAG CTC GAT GTA ACG TGC AGT TAA CGC CCA TGT CTC CTG GCT CAA GTT TGC (SEQ ID NO:1) and Reverse: CCT ACT AAC AGA TAC GCT ATG CAG GAC TCT GGA TTG CCC TGT TGG CAT GGC TGA AAT AA (SEQ ID NO:2). The final PCR reaction concentration mix was: 1× Herculase Hotstart Buffer (Stratagene, La Jolla, Calif.), 0.2 mM dNTPs, 25 ng/μl of each primer, 0.15 U/μl Hotstart High Fidelity DNA Polymerase (Stratagene), 2 μl of genomic DNA, and ddH$_2$O to 10 μl. PCR conditions were: 94° C. for 2 min, then 35 cycles of: (94° C. for 45 min, 61° C. for 45 min, 72° C. for 2 min 30 sec) with a final elongation step of 72° C. for 10 min. PCR products were confirmed by gel electrophoresis and cotransformed into yeast along with the universal vector (Chen and Gould, 2004, *Biotechniques* 37: 383-388).

Genotyping of Apc$^{am1137/+}$ Animals. Two PCR/restriction enzyme digestion methods were developed to genotype the mutant SNP site of the Apc$^{am1137}$ allele. One amplicon results in the mutant allele being cut by NheI and one results in the wild type allele being cut by HindIII. Both work by introducing the restriction enzyme recognition sites into the primers. These complementary methods control for incomplete digests.

The primer sequences were as follows: for the NheI amplicon, Forward: GGA AGA CGA CTA TGA AGA TGG (SEQ ID NO:3) and Reverse: TGC CCT GTA CTG ATG GAG (SEQ ID NO:4). For the HindIII amplicon, Forward: AAT AAC GTT CAC TGT AGT TGG TAA GCT (SEQ ID NO:5) and Reverse: AGG CAA TCA AGA AGC CAG AA (SEQ ID NO:6).

MicroCT and Endoscopy. Normal chow was replaced with a non-solid diet the night before microCT imaging. Anesthesia was administered through the regulated flow of isoflurane vapor (1-2%) through a nose cone. The colon was flushed with a warm PBS enema (40 cc). The colon was insufflated with air (20-40 cc), and microCT and endoscopic images were acquired on a Siemens MicroCAT-2 scanner. Acquisition proceeded for 8 minutes (80 kVp, 500 μA, 400 steps, 1 frame/view, 360 degree rotation, 93×93×100 μm voxel size) and reconstruction was done via Shepp-Logan filtered, back-projection. Amira (v 4.1, TGS, Inc., San Diego, Calif.) software was used for 2- and 3-dimensional image visualization and media production. Ex vivo imaging of excised colons was accomplished by filling the colon with barium as a contrast agent and tying off the ends.

Endoscopy was performed using an EG-1870K 6.0 mm color CCD chip videogastroscope and an EPK 1000 videoprocessor (Pentax Medical, Montvale, N.J.). The image was captured on the workstation and photographed with an Olympus Camedia C-5050ZOOM digital camera using automatic exposure.

Somatic ENU treatment. ENU was dissolved in 95% EtOH and measured with a spectrophotometer at $OD_{398nm}$ to obtain a final concentration of 1 mg/ml. Either the ENU solution or 95% EtOH was injected intraperitoneally into 13-20 day old rats at 18 or 40 mg/kg of body mass. Treated animals were isolated in a laminar flow hood for at least three days before being returned to normal housing.

Immunofluorescence. Immunofluorescence was performed by first de-waxing the slides in xylene, rehydrating through an EtOH series, and boiling for 25 min in 0.01M citrate buffer, pH 6.0. After washing in PBS, slides were incubated for 1 hour at 37° C. with the following primary antibodies: anti-mouse β-catenin-TRITC mAb (Transduction Laboratories, Lexington, Ky.) at 1:200 and anti-human Ki-67 pAb (Novacastra, Newcastle, UK) at 1:100. After washing in PBS, 0.1% Tween-20, slides were incubated for 1 hour at 37° C. with the following secondary antibodies: goat anti-mouse Alexafluor-594 (Molecular Probes, Eugene, Oreg.) at 1:200 and donkey anti-rabbit Alexafluor-488 (Molecular Probes) at 1:200.

After washing in PBS, 0.1% Tween-20, slides were incubated for 5 min with DAPI, mounted, and sealed. Images were taken with a Zeiss Axiocam HRm camera mounted on a Zeiss Axiovert 200M inverted microscope. Images were taken with Axiovision software (v4.5.0.0).

Methylene Blue Staining. 0.5% methylene blue was heated until all particles were dissolved, then cooled to room temperature. Fixed intestines were placed into the methylene blue for 15-30 seconds, then washed in 70% methanol for 5-10 minutes.

Sanger Sequencing. Primers were digested away from the PCR amplicon of interest with Exonuclease I by adding the following mix to the PCR: 3.3 U/µl of Exonuclease I (Epicentre, Madison, Wis.), 1.7 U/µl of shrimp alkaline phosphatase (Roche, Basel, Switzerland), and $ddH_2O$ to 1.5 µl. Reactions were incubated at 37° C. for 45 min and heat inactivated at 85° C. for 15 min. Big Dye Terminator Mix (Applied Biosystems, Foster City, Calif.) and 5× sequencing buffer (Applied Biosystems) were added at a 2:3 ratio, along with 6.6 mM sequencing primer. The reaction was then purified on Sephadex G-50 columns (Roche) and submitted to the UW-Madison Biotechnology Center. Samples were run on an Applied Biosystems 3730×1 automated DNA sequencing instrument and results were analyzed using the DNAstar (Madison, Wis.) software.

Pyrosequencing. Formalin-fixed tumors were excised under a dissecting microscope to minimize contamination from non-tumor tissue. The bottom one-fourth of the polyp including the muscularis and any surrounding hyperplastic villi were excluded to enrich for tumor regions likely to exhibit Apc loss and β-catenin upregulation. Excised tissue was incubated overnight in distilled water at 65° C. to reverse formalin cross-links. 100 mM NaOH was added to a final concentration of 50 mM and samples were incubated at 95° C. for at least four hours. Tris-HCl, pH 5.5 was then added to neutralize the solution and the samples were briefly centrifuged. The final PCR mix concentrations were as follows: 1× GoTaq clear buffer, 1.2 mM $MgCl_2$, 0.2 mM dNTPs, 264 pM of each primer, 0.6 U of GoTaq Flexi (Promega, Madison, Wis.), 8 µl of DNA, and $ddH_2O$ to 50 µl. The PCR cycling profile was: 94° C. for 3 min, followed by 50 cycles of: (94° C. for 15 sec, 57° C. for 1 min 30 sec, 72° C. for 2 min) with a final elongation step of 72° C. for 10 min.

Pyrosequencing was performed according to the manufacturer's protocols using Pyro Gold Reagents on a PSQ96MA machine and PSQ 96MA v2.1 software (Biotage, Uppsala, Sweden). 40 µl of PCR product were used per well and only sequence reads with single base peak heights of over 120 units were included.

Primer sequences were as follows: for the $Apc^{am1137}$ SNP, Forward: ATG TGA ACC AGT CTT TGT GTC AG (SEQ ID NO:7); Reverse (biotinylated): ATG CTG TTC TTC CTC AGA ATA ACG (SEQ ID NO:8); Sequencing: GGA AGA CGA CTA TGA AGA T (SEQ ID NO:9). For the p arm SNP (dbSNP ss48531311), Forward: GTG GAA ACG AAG CAT CAT TCT GA (SEQ ID NO:10); Reverse (biotinylated): TGC TGT TCT AAA TTG CAC GTT TAC (SEQ ID NO:11); Sequencing: CGT ATT GGG TTG TGA GA (SEQ ID NO:12). For the q arm SNP (dbSNP ss48531727), Forward (biotinylated): TCA AAC AGA AGG CAG TTT ATT CAG (SEQ ID NO:13); Reverse: GGG GGT AAA ATA ATA TGC CGA GA (SEQ ID NO:14); Sequencing: TCT TAG TAA TGT ACC AGA TG (SEQ ID NO:15).

An LOH/MOH cutoff value of 32.8% was determined by adapting the normal mixture technique from Shoemaker et al., 1998, *Proc. Nat. Acad. Sci. USA* 95: 10826-10831. Tumor data (n=114) were considered to arise either from an LOH normal component or an MOH normal component, according to some mixing probability. Control data came from a known MOH component (normal Pirc epithelium n=10). Then, using the fitted mixture model, a critical signal intensity value c was determined so that Prob[intensity>c|LOH]=0.05. In the estimated normal mixture, the LOH component had mean 16.2 and standard deviation 8.0; the MOH component had mean 43.2 and standard deviation 3.5; and an estimated fraction 84% of tumors were LOH. From this the critical signal value was c=32.8. Modes of the likelihood surface at the boundary of the parameter space were avoided. Computations were done in R (R Development Core Team, 2005, R: A language and environment for statistical computing; available at http://www.R-project.org).

Identification of the $Apc^{am1137}$ Mutation. The mutation was generated by treating a male Fischer-344 rat with ENU, and mating it to a female Fischer-344 rat. The resulting progeny carried a subset of the mutations induced in the original male's sperm. The DNA was then extracted from these progeny (founders) and screened for mutations.

FIG. 1 depicts how a segment of 2530 base pairs of exon 15 of the rat Apc gene from genomic DNA in the offspring of mutagenized Fisher-344 inbred rats was screened. The method of screening for the mutant rats using a universal vector gap repair yeast truncation assay is described in Chen and Gould, 2004, *Biotechniques* 37: 383-388.

A 2.5 kb portion of the Apc gene was PCR amplified from the progeny and inserted into a yeast vector. The vector was transformed into yeast and plated on Ade2-indicator plates. If the Apc-Ade2 fusion transcript was normal, a large white colony was formed. If the fusion transcript was interrupted by an ENU-induced stop codon in Apc, then the loss of Ade2 allows the accumulation of a red substrate in the yeast, giving rise to a small red colony. The Pirc founder rat exhibited a yeast plate with ~50% red colonies, indicating that a heterozygous stop codon mutation had been induced in the 2.5 kb region of the APC gene by ENU. The wild-type sibling rat used for comparison had a wild-type distribution of ~13% red colonies (due to background "noise").

Figure 2:
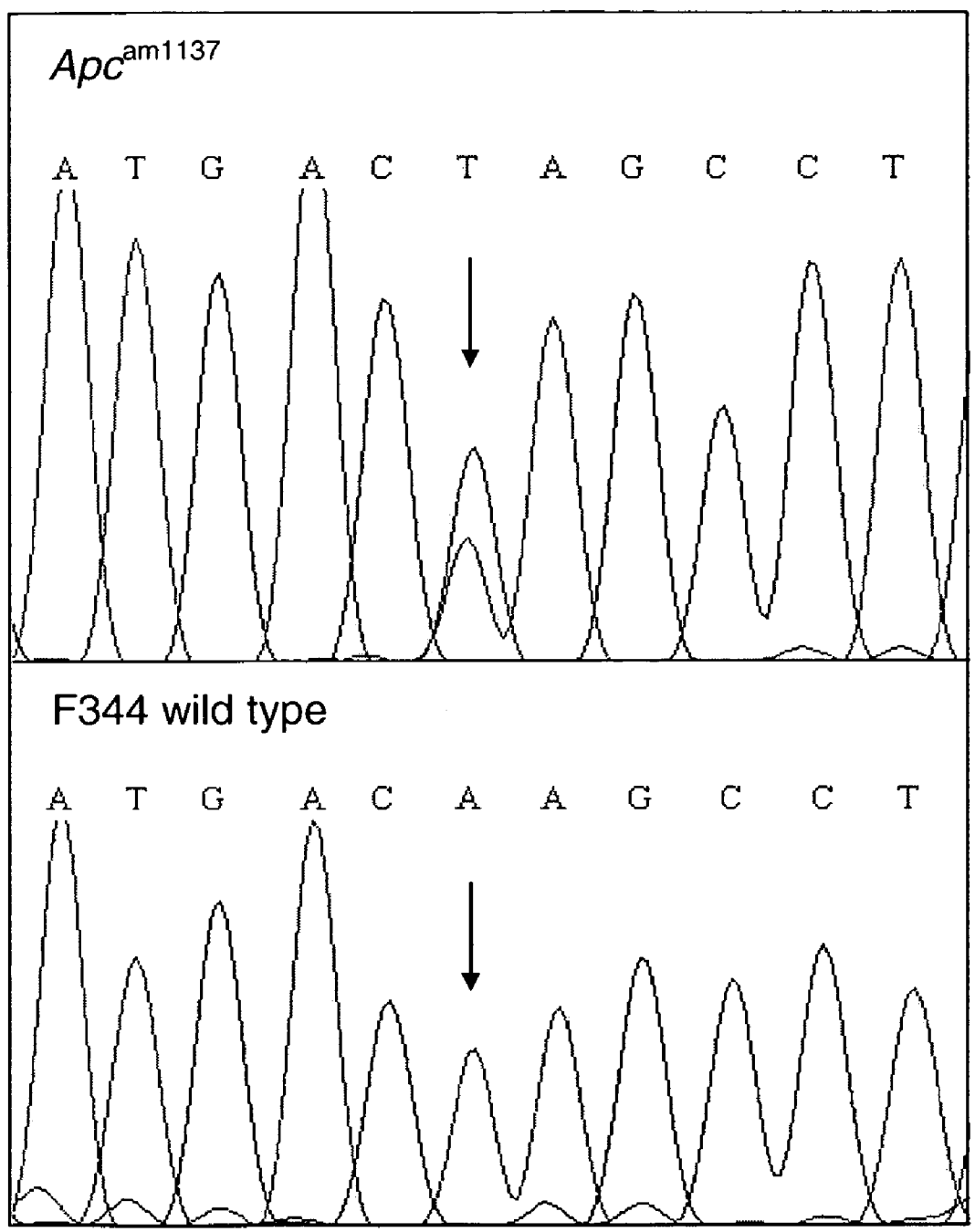
FIG. 2 depicts sequence trace of the founder rat showing heterozygosity for the A→T transversion at nucleotide 3409 of Apc (top) compared to a wild-type littermate (bottom).

Screening of 1360 progeny yielded a single mutant with an A to T transversion changing a lysine to a stop codon at codon 1137 (see $Apc^{am1137}$ in FIG. 2). The founder male successfully transmitted the mutation to progeny. Ten of the resulting mutant N1 animals were brother-sister mated and their offspring confirmed that the Pirc allele is homozygous lethal. Necropsy of three N1 Pirc heterozygotes, two at 90 days and one at 120 days of age, identified an average of 5 visible adenomatous polyps in the colon, while three wild type age-matched littermates were tumor-free.

The founder Pirc male rat harbored a heterozygous point mutation at nucleotide 3409 of Apc, creating a K→X$^{am}$ (AAG→TAG) change at codon 1137 (FIGS. 2 and 3). No other mutations were found after sequencing the entire coding region and intron-exon junctions 5' of the mutation. This allele was named Apc$^{Pirc}$ or Apc$^{am1137}$. The predicted APC protein would be truncated at the third amino acid of the second 15-amino acid β-catenin binding domain (FIG. 3), which is highly conserved among vertebrates.

FIG. 3 shows a cross-species alignment of 50 amino acids surrounding the Pirc mutation (SEQ ID NOs: 7-23). Note the conserved 15 amino acids (boxed) that indicate the β-catenin binding domain The Pirc mutation (K to X, i.e. lysine to a stop codon) is located in that β-catenin binding domain.

Figure 4:
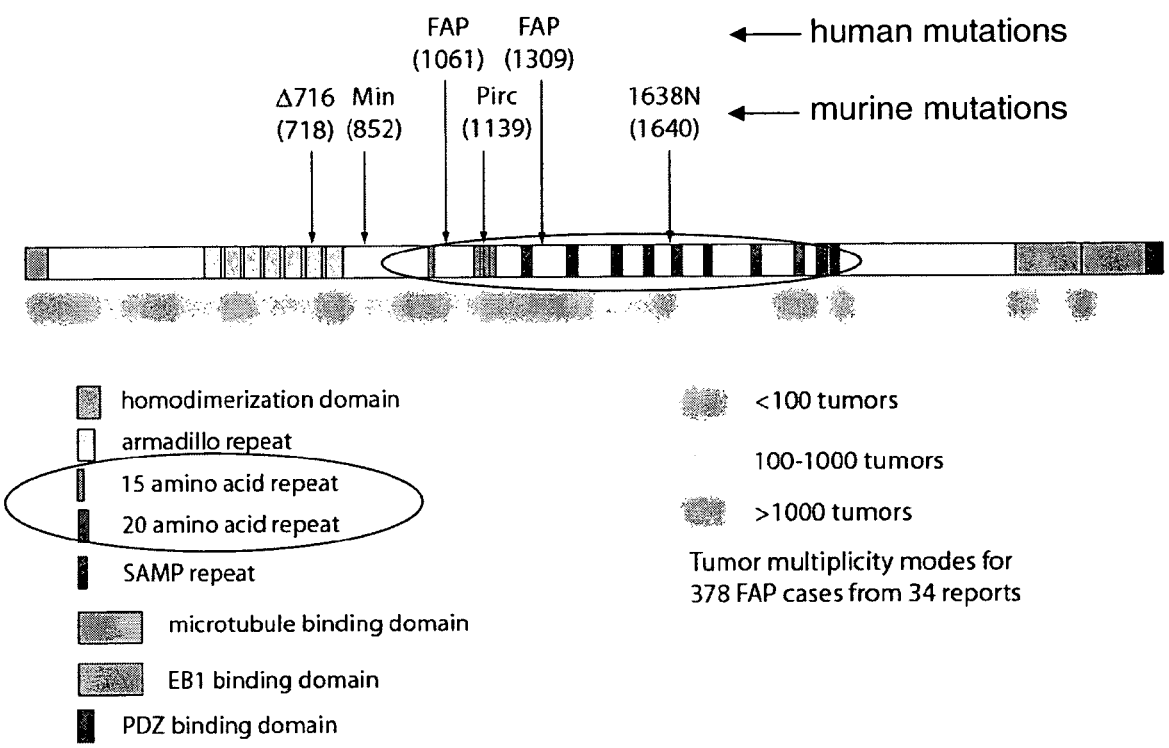
FIG. 4 is a schematic diagram of the human APC (hAPC) protein domains.

A diagram of the known domains of the human Apc protein is shown in FIG. 4 with the positions of the most well-known mutations in human and mouse (and the mutant Pirc rat, this invention) marked across the diagram. The 15 amino acid and 20 amino acid binding repeats circled are the beta-catenin binding regions. It is possible that loss of Apc function results in upregulation of the oncogenic beta-catenin protein, inducing tumors. The Pirc rat therefore has a nonsense mutation that results in truncation of the protein and loss of almost all of the beta-catenin binding domains.

Also shown in FIG. 4, under the protein diagram, is a graph of modal tumor multiplicities from human familial adenomatous polyposis (FAP) patients as compared to where their truncating mutation lies. Thus, the Pirc rat mutation lies in an area analogous to a fairly severe FAP phenotype.

The Apc$^{am1137}$ Mutation is not Lethal. Apc$^{am1137/+}$ animals were intercrossed on either an inbred F344/NTac (F344) or a [F344×WF/NHsd (WF)] F1 background, to determine whether this Apc$^{am1137}$ mutation is homozygous lethal. No homozygous mutants were obtained out of 71 total progeny, with heterozygotes and wild-type progeny exhibiting a 2:1 Mendelian ratio (49:22). Thus, the Apc$^{am1137}$ allele is homozygous lethal on two genetic backgrounds. In the formal possibility that this lethality is caused by a second ENU-induced mutation, it would lie within 2.5 cM (95% CI) of the Apc$^{am1137}$ mutation.

Consideration of the possibility that lethality is due to a second mutation X linked to Pirc. The data taken together strongly support the contention that Pirc is homozygous lethal; however, the possibility that the lethality is due to a second mutation X linked to Pirc was considered. If X is r recombination units from Pirc, the probability of observing a Pirc homozygote at the kth generation, conditional on non-XX parents (P(Pirc/Pirc|non-XX)), is $$\frac{0.5a_k(r - r^2/2) + 0.25b_k + 0.5a_k b_k}{0.75a_k + b_k + 2a_k b_k}$$

where $a_k = (1-r)^k$ and $b_k = 1 - a_k$.

Using these probabilities, 95% confidence intervals for r can be calculated. For example, consider the hypothesis test H0: r>r0 against HA: r<r0. Each value of r0 determines P(Pirc/Pirc|non-XX), the expected proportion of Pirc homozygotes. Using this expected proportion, a Binomial test can be done assuming zero Pirc homozygotes are observed. By inverting the test (Bickel and Docksum 2001, *Mathematical Statistics Vol. I*, 2nd edition, Prentice-Hall, N.J.), a conservative 95% confidence interval for r is found. When k=1 and n=71, the 95% confidence interval for r is (0, 0.0243).

Tumor phenotype segregates perfectly in 56 carriers and 23 non-carriers. Suppose the phenotype is due to a linked loci X, r recombination units from Pirc. The Binomial probability of observing no recombinations in 79 trials is 0.046 for r=0.038 and 0.00969 for r=0.057.

The phenotype of F344-Apc$^{am1137/+}$ animals at the N1-N3 generations was analyzed. Around 11 months of age, males became moribund from rectal bleeding and weight loss. By contrast, females carrying this mutation have survived to over 14 months of age with no external signs of disease. Dissections at ages ranging from 88 to 397 days revealed multiple neoplasms in the small intestine and colon of both male and female heterozygotes.

The Pirc phenotype segregated perfectly with the Apc$^{am1137}$ allele in 56 carriers and 23 non-carriers. There is less than a 5% chance to observe this association if the phenotype were caused by a separate mutation more than 3.8 cM from Apc$^{am1137}$. Full necropsies of Pirc animals uncovered benign epidermoid cysts, but no other neoplasms or metastases. No significant differences in the multiplicity or phenotype of intestinal tumors were seen between successive backcross generations of the Pirc kindred on the inbred F344 background, indicating that any effects of ENU-induced modifying alleles are relatively minor.

Tumor multiplicities were determined for both adenomas and microadenomas (neoplasms less than 0.5 mm in diameter). A significant dependence on gender was observed, with males developing more of both types of tumor in all regions of the intestinal tract. There was also a monotonic increase in tumor multiplicity with age, reaching an average of 14 colonic adenomas in males and 9 in females over eight months of age (Tables 3 and 4).

Shown in Table 3 are the tumor multiplicities in Pirc rats. Colonic microadenoma multiplicities could not be accurately measured without histopathological confirmation and were excluded from these analyses. Neoplasms less than 0.5 mm in size were classified as microadenomas.

TABLE 3

Tumor multiplicities in Pirc rats

| Background | Sex | Age (mo) | N | Colonic polyps, mean ± SD | Lesions in small intestine, mean ± SD | |
|---|---|---|---|---|---|---|
| | | | | | Adenomas | Microadenomas |
| F344-Pirc | Male | 3 | 5 | 2 ± 1 | 7 ± 9 | 21 ± 20 |
| | | 4-6 | 10 | 8 ± 3 | 14 ± 5 | 88 ± 64 |
| | | 7-13 | 17 | 14 ± 8 | 22 ± 9 | 178 ± 116 |
| | Female | 3 | 5 | 3 ± 2 | 0 ± 0 | 1 ± 2 |
| | | 4-6 | 11 | 5 ± 3 | 2 ± 2 | 19 ± 29 |
| | | 7-13 | 6 | 7 ± 5 | 4 ± 5 | 35 ± 44 |

TABLE 3-continued

Tumor multiplicities in Pirc rats

| Background | Sex | Age (mo) | N | Colonic polyps, mean ± SD | Lesions in small intestine, mean ± SD | |
|---|---|---|---|---|---|---|
| | | | | | Adenomas | Micro-adenomas |
| F344-Pirc, ENU treated | Male | 7 | 3 | 79 ± 11 | 57 ± 13 | 665 ± 103 |
| (F344-PircxWF)F1 | Male | 6 | 1 | 1 | 0 | 6 |
| | | 10-14 | 3 | 1 ± 1 | 3 ± 2 | 8 ± 6 |
| | Female | 6 | 5 | 1 ± 1 | 1 ± 1 | 1 ± 1 |
| | | 10-12 | 2 | 1 ± 0 | 1 ± 1 | 0 ± 0 |
| (F344-PircxSD)F1 | Male | 7 | 3 | 2 ± 1 | 2 ± 1 | 14 ± 11 |
| | Female | 7 | 5 | 1 ± 1 | 1 ± 1 | 1 ± 1 |

Shown in Table 4 is the estimation of age and gender effects on tumor multiplicity. A Poisson regression was used to estimate the effects of age and gender on tumor multiplicity in F344 Pirc animals. The estimated age and gender coefficients are shown in Table 4 along with associated p-values and 95% confidence intervals for colon (C), small intestine (SI), and small intestinal microadenomas (SITm). The results show that age and gender significantly affect each phenotype. The results were qualitatively similar when a Gaussian regression was used on a square root transformed phenotype. Results are shown for Poisson regression.

TABLE 4

Estimation of age and gender effects on tumor multiplicity

| | C | SIT | SITm |
|---|---|---|---|
| Age Coefficient, p-value | 0.005, <0.005 | 0.004, <0.005 | 0.006, <0.005 |
| 95% Confidence Interval | (0.004, 0.006) | (0.003, 0.005) | (0.0059, 0.0066) |
| Gender Coefficient, p-value | 0.624, <0.005 | 2.137, <0.005 | 1.742, <0.005 |
| 95% Confidence Interval | (0.403, 0.845) | (1.808, 2.467) | (1.639, 1.846) |

The incidence and multiplicity of colonic tumors is higher in the F344-Pirc rat than in carcinogen treated wild-type F344 rats or the Min mouse. Importantly, the Pirc rat addresses one of the major drawbacks of all genetic mouse models of intestinal cancer: the prominence of tumors in the small intestine. The ratio of tumor multiplicities in the colon to that in the small intestine in Pirc rats averages 1:1. By contrast, most lines of B6-Min mice have an average ratio of about 1:40 (Table 1). The estimated polyp incidence in the small intestine of human Familial Adenomatous Polyposis (FAP) patients ranges from 58-74% at first endoscopy and approaches 100% by 70 years (Bulow, 2004, Gut 53: 381-386), with multiplicities exceeding 80 in 17% of patients monitored with video capsule endoscopy. Thus, the distribution of intestinal tumors in the Pirc rat resembles that in FAP patients.

Figure 5:
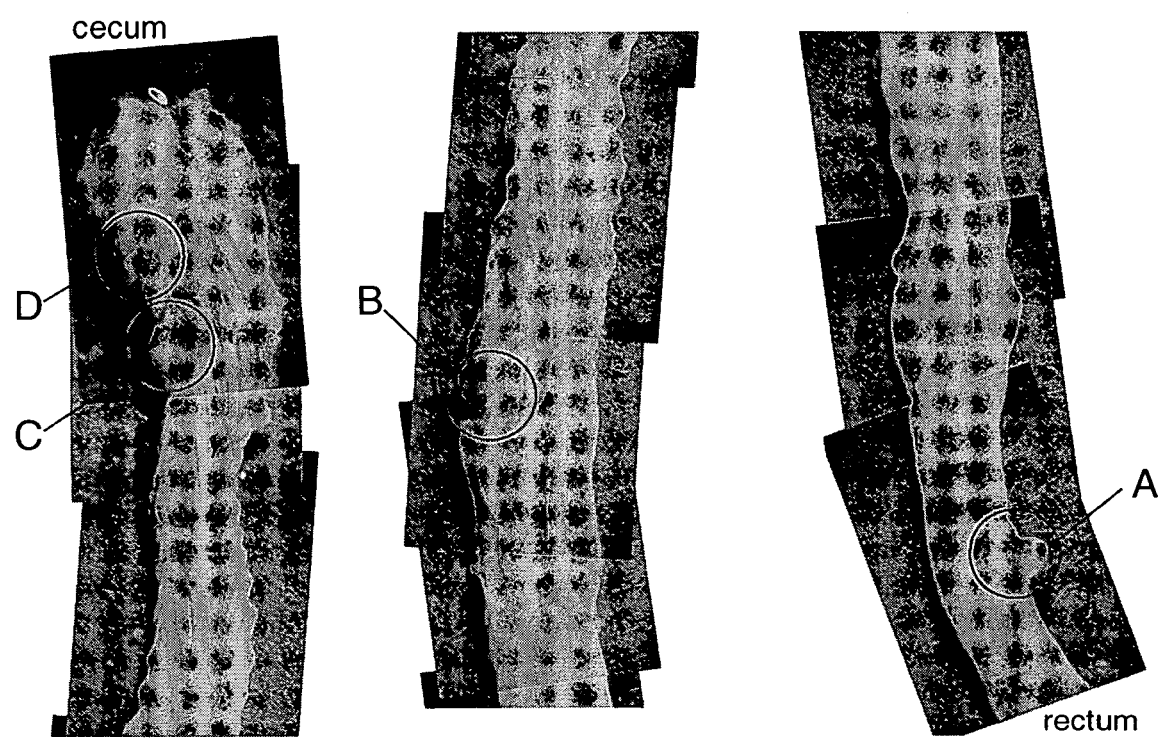
FIG. 5 shows images of colonic tumors that have developed in Pirc rats.

Thus, it was unexpectedly discovered that the rat mutation in Apc results primarily in colon tumors (FIG. 5), as it does in humans. FIG. 5 depicts tumors (shown in circles labeled A-D) developed in the colon. The expected result was tumor development similar to the Min mouse, which has a mutation in Apc and has tumors that occur primarily in the small intestine.

Figure 6:
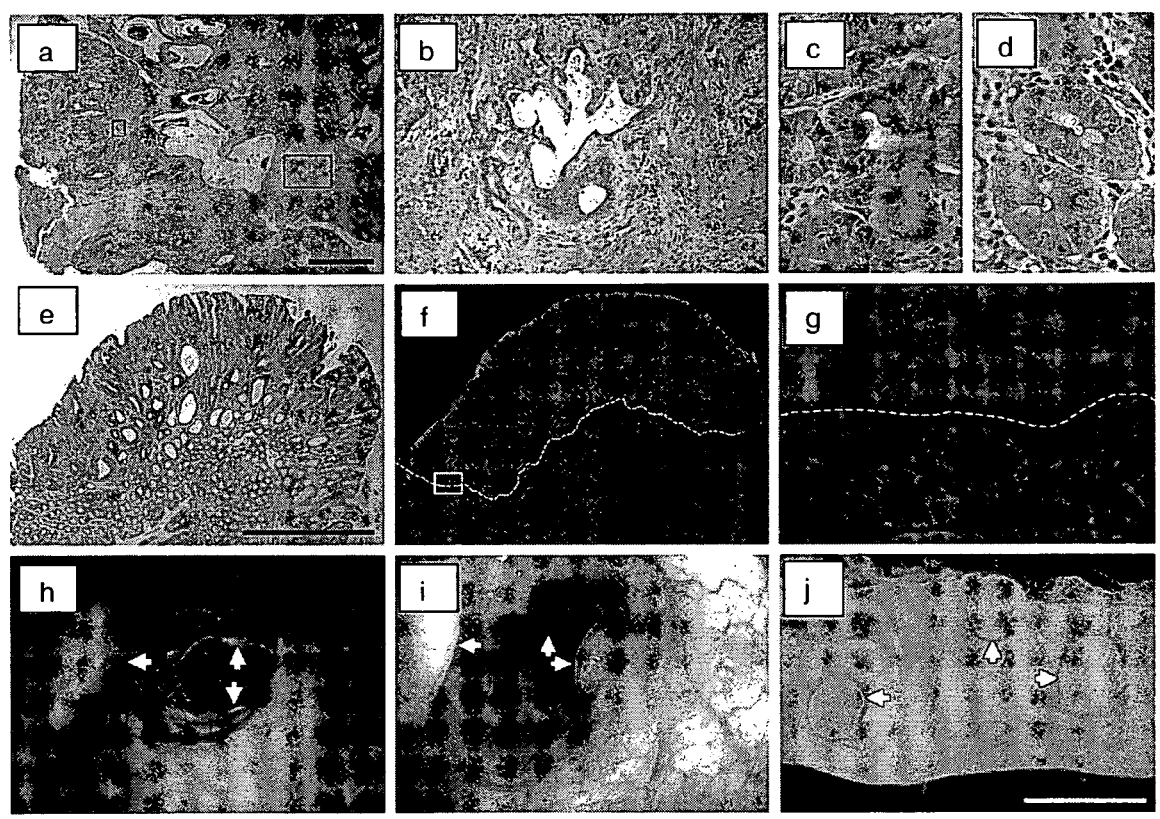
FIG. 6 depicts images showing the histological and gross appearance of Pirc tumors.

The histological and gross appearance of Pirc tumors was examined, and is depicted in FIG. 6. Thus, FIG. 6(a) shows H&E images of a focal adenocarcinoma with high-grade dysplasia. (b) Enlargement of the larger rectangle in panel a, showing invasion into the stalk. (c) Enlargement of the smaller rectangle in panel a, showing high grade dysplasia, as compared to normal crypts (d), from the same section. (e) H&E of a peduncular colonic adenoma. (f) β-catenin (red in original) and DAPI (blue in original) immunofluorescence of the same tumor. The dashed line delineates dysplastic tissue, i.e. tumor proper (above) and hyperplastic but non-tumorigenic tissue (below). (g) Magnification of the rectangle shown in panel f. (h, i, j) MicroCT, endoscopic, and dissection views, respectively, of three colonic tumors in an 11-month old F344 Pirc male. Scale bars: a and e, 1 mm; j, 1 cm.

To characterize the intestinal lesions, histological examinations of sections of paraffin-embedded formalin-fixed tumors were performed. The neoplasms were identified as adenomas, adenocarcinomas in situ, or focal adenocarcinomas with invasion into the stalk (FIG. 6a-d). The histopathology and morphology of the tumors closely resembled that of the human. Tumors in the small intestine usually were flat, while colonic tumors were peduncular. Adenomas varied in size, frequently reaching 1 cm in diameter in older animals. Immunofluorescent staining of tumors revealed nuclear and cytoplasmic accumulation of P-catenin within dysplastic (abnormal) cells (FIG. 6e-g) as well as upregulation of the proliferation marker Ki-67 (data not shown).

To determine whether longitudinal in vivo studies of intestinal tumorigenesis can be carried out, a 334-day old Pirc rat was anesthetized and its tumors visualized by endoscopy. A 6 mm-diameter endoscope provided clear images of three tumors with diameters 5.3 mm, 5.7 mm, and 6.8 mm. The same tumors were identified in three-dimensional microCT images and confirmed upon dissection (FIG. 6h-j). This proof of principle paves the way for investigation into the sensitivity and specificity of endoscopy versus virtual colonoscopy. Endoscopy also enhances the statistical power of drug and genetic studies, minimizing the numbers of tumor-bearing rats required. Longitudinal studies of tumor progression and regression can be related to molecular profiles through endoscopic pinch biopsies of individual tumors.

The issue of whether genomic instability is necessary in early colonic neoplasms was also addressed. First, loss of heterozygosity at the $Apc^{am1137}$ site on the inbred F344 background was quantitatively assayed by a novel Pyrosequencing assay. A majority of F344 tumors in the colon (87%, 34/39) and small intestine (100%, 24/24) showed loss of heterozygosity (LOH) of the wild-type Apc allele at codon 1137.

The metacentric karyotype of the rat was used to address whether the function of the wild-type Wistar-Furth (WF) allele of Apc in (F344×WF) Pirc animals is lost through elimination of the entire WF chromosome, through homozygosis via somatic recombination, or through another genetic or epigenetic process. Polymorphic single nucleotide polymorphisms (SNPs) on the p and q arms of chromosome 18 were assayed in tumors and in adjacent normal, heterozygous tissue from (F344×WF) F1 and F2 animals (FIG. 7).

Figure 7:
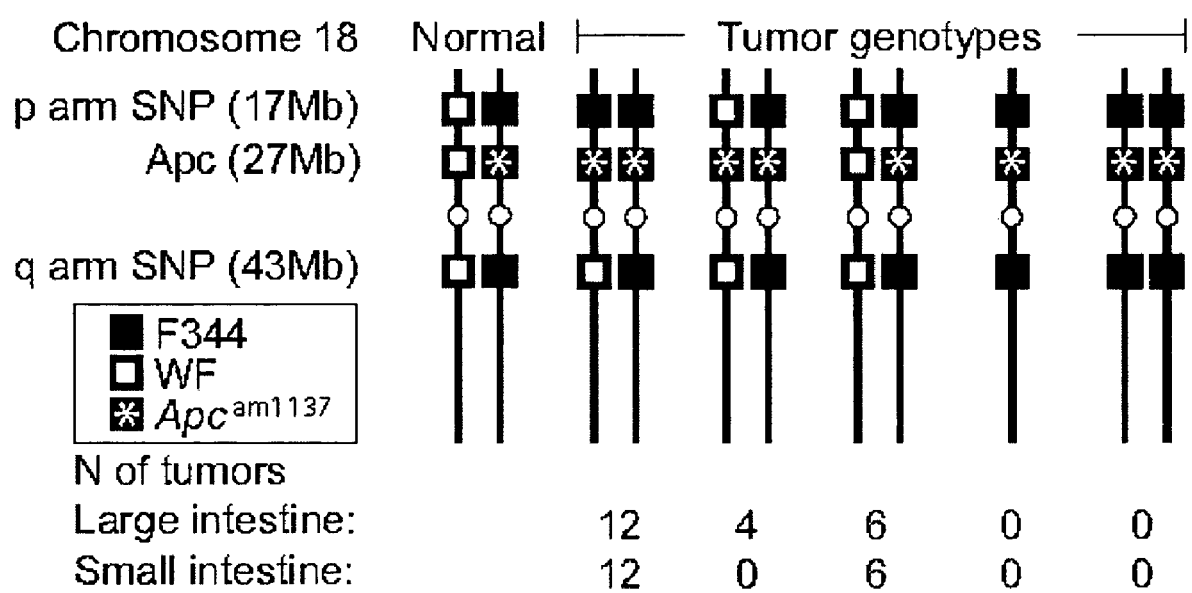
FIG. 7 illustrates LOH analysis for chromosome 18 on (F344×WF) F1 and F2 tumors.

Shown in FIG. 7 is LOH analysis for chromosome 18 on (F344×WF) F1 and F2 tumors. The three SNPs tested, ss48531311 (17 Mb) and $Apc^{am1137}$ (27 Mb) on the p arm and ss48531727 (43 Mb) on the q arm, were all heterozygous in the normal tissue. The centromere (open circle) lies at approximately the 38 Mb position. LOH status at each SNP was assayed by quantitative Pyrosequencing. Five possible tumor genotypes are given (left to right): LOH involving only the two loci on the p arm, LOH involving only $Apc^{am1137}$, maintenance of heterozygosity at all three loci, hemizygosity for both arms (as assessed by aCGH), and homozygosis for all three loci.

If both chromosome arms exhibit LOH, whole chromosome loss with or without reduplication would be indicated. By contrast, if only one arm undergoes LOH, somatic recombination or terminal deletion would be supported. None of 22 colonic or 18 small intestinal tumors showed loss of both arms of the WF homolog. Of 16 colonic and 12 small intestinal tumors with arm-specific LOH, all loss events involved the Apc locus on the p arm, extending at least 10 Mb distal in the majority of tumors. In all cases of LOH, the WF allele was lost while the F344 allele was maintained.

Figure 8:
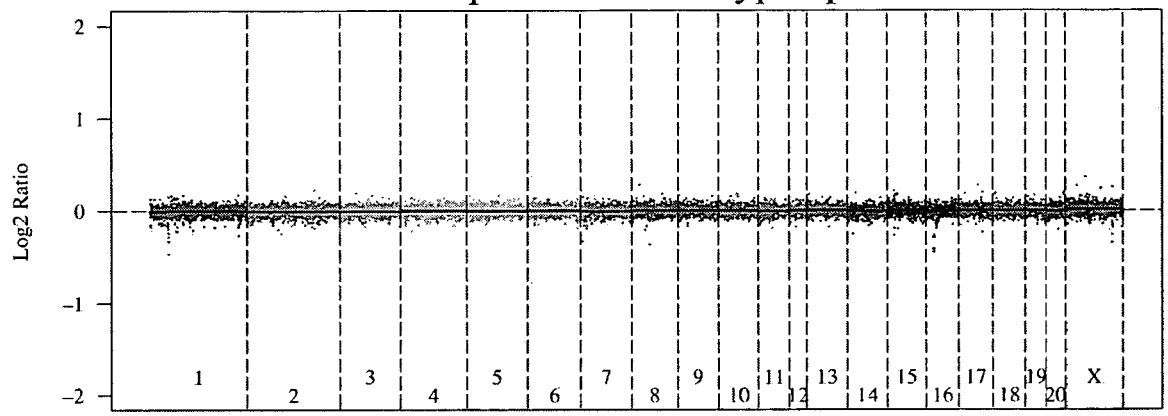
FIG. 8 illustrates aCGH analysis of colon tumor and normal genomes.
Figure 8:
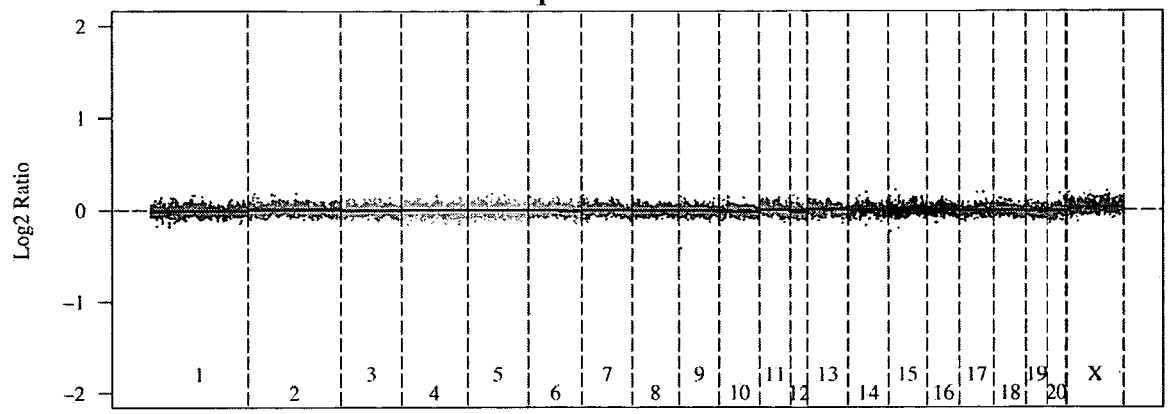
Figure 8:
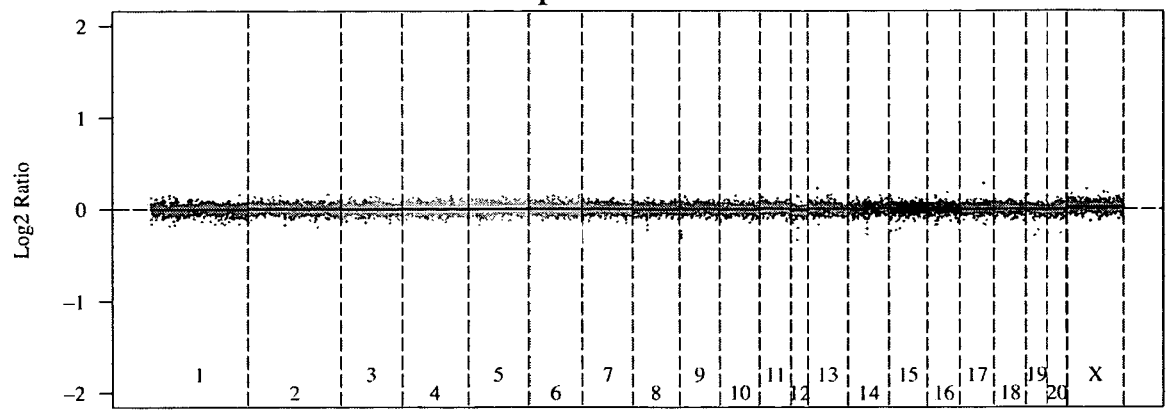

Array-based Comparative Genomic Hybridization (aCGH) analysis. The possibility of extended deletion of the q arm was tested by array comparative genomic hybridization (aCGH) analysis of two F344 colonic adenomas showing LOH at Apc (FIG. 8). Immediately following necropsy, DNA was extracted from approximately 50 mg each of tumor and spleen tissue using the Qiagen DNeasy tissue kit. Comparative genomic hybridizations were performed by Nimblegen Systems (Madison, Wis.) in their Iceland manufacturing facilities using the Nimblegen RGSC 3.4 isothermal rat aCGH chip with 385,000 unique sequence features and a median probe density of 5303 bp. Tumor and Pirc spleen DNA from the same animal were labeled with Cy5 or Cy3 and reciprocal hybridizations were performed for both tumor samples. Pirc spleen DNA was also hybridized against wild-type spleen DNA. CGH plots were generated using NimbleScan software and the data analyzed using SignalMap v1.8.

No allelic imbalance was detected over the entire genome of these tumors. FIG. 8 shows aCGH analysis of colon tumor and normal genomes. Plots show the $\log_2$ ratio (y axis) calculated over 250 kb windows for the entire rat genome (RGSC 3.4, November 2004 build) by chromosome (x axis). The Pirc spleen and tumor samples were hybridized against each with Cy5 vs Cy3 labeling in both orientations. Tumors were determined to involve LOH by Pyrosequencing and calculated to be 70-80% pure. FIG. 8(a) shows a Pirc spleen genomic DNA compared to wild-type spleen DNA. No significant difference is seen between the two, indicating the germline copy number variation. FIG. 8(b, c) shows Pirc colon tumor genomic DNAs compared to spleen DNA from the same animal. Only one of the two labeling orientations is shown for each tumor. No statistically significant variation from the spleen was seen in either tumor sample.

The rat kindred for familial colon cancer of this invention has several features that can fuel investigations of colon cancer: the location of tumors resembles that in the human; the surface density of early neoplasms can reach the same level as in human FAP individuals; dominant polymorphic modifiers exist in rat genomes; and imaging by microCT and classical endoscopy gives access to statistically powerful longitudinal studies of tumor progression and regression.

Shown in Table 5 is an example of the use of a Pirc rat for screening a compound for carcinogenesis inhibitory activity. The effect of celecoxib on intestinal tumor multiplicity in F344 Pirc rats was tested. At about 40 days of age, Pirc rats backcrossed with F344-Tac and F334 control rats were fed celecoxib at 1200 ppm diet. The rats were killed at about 22 weeks of age (about 150-160 days of age). Necropsy was performed to identify 1-2 mm tumors in the intestines.

TABLE 5

Use of the Pirc rat for screening the efficacy of celecoxib as a compound for carcinogenesis inhibitory activity

| | | Control diet | Celecoxib 1200 ppm diet | Relative reduction in number of tumors |
|---|---|---|---|---|
| Male Pirc rat | Average total number of tumors | 10.6 | 2.6 | 76% |
| | Average number of tumors in small intestine | 7.5 | 1.3 | 82% |
| | Average number of tumors in large intestine | 3.1 | 1.2 | 61% |
| | n = | 8 | 9 | |
| Female Pirc rat | Average total number of tumors | 2.0 | 1.0 | 50% |
| | Average number of tumors in small intestine | 0.6 | 0.9 | n/a |
| | Average number of tumors in large intestine | 1.4 | 0.1 | 93% |
| | n = | 10 | 9 | |

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters normally encountered in clinical prevention and therapy, obvious to those skilled in the art, are within the scope of this invention. All publications, patents, and patent applications cited herein are incorporated by reference in their entirety for all purposes.

What is claimed is:

1. A rat comprising a truncated Apc protein, the truncated protein being encoded by an Apc gene, wherein one allele of the Apc gene comprises SEQ ID NO: 16, the rat being heterozygous for the allele.

2. The rat of claim 1, having a higher rate of tumor development in its colon compared to a wild-type rat.

3. The rat of claim 1, wherein the allele comprising SEQ ID NO: 16 is present on a genetic background of a genetically inbred rat line.

4. The rat of claim 1, wherein the allele comprising SEQ ID NO: 16 is inherited from a genetic parent.

5. An isolated nucleic acid comprising the nucleotide sequence of Rat Genome Database ID No. 1554322 (SEQ ID NO:16).

6. A vector comprising the isolated nucleic acid sequence of claim 5.

7. A rat embryo comprising a truncated Apc protein, the truncated protein being encoded by an Apc gene, at least one of the alleles of the Apc gene comprising SEQ ID NO: 16.

8. The rat of claim 3, wherein the genetically inbred rat line is Fischer-344.

* * * * *

SEQUENCE LISTING

<160> NUMBER OF SEQ ID NOS: 23

<210> SEQ ID NO 1
<211> LENGTH: 60
<212> TYPE: DNA
<213> ORGANISM: Artificial
<220> FEATURE:
<223> OTHER INFORMATION: Long-range PCR forward primer

<400> SEQUENCE: 1
ggccatcgat agctcgatgt aacgtgcagt taacgcccat gtctcctggc tcaagtttgc        60

<210> SEQ ID NO 2
<211> LENGTH: 59
<212> TYPE: DNA
<213> ORGANISM: Artificial
<220> FEATURE:
<223> OTHER INFORMATION: Long-range PCR reverse primer

<400> SEQUENCE: 2
cctactaaca gatacgctat gcaggactct ggattgccct gttggcatgg ctgaaataa         59

<210> SEQ ID NO 3
<211> LENGTH: 21
<212> TYPE: DNA
<213> ORGANISM: Artificial
<220> FEATURE:
<223> OTHER INFORMATION: Forward primer for NheI amplicon

<400> SEQUENCE: 3
ggaagacgac tatgaagatg g                                                  21

<210> SEQ ID NO 4
<211> LENGTH: 18
<212> TYPE: DNA
<213> ORGANISM: Artificial
<220> FEATURE:
<223> OTHER INFORMATION: Reverse primer for NheI amplicon

<400> SEQUENCE: 4
tgccctgtac tgatggag                                                      18

<210> SEQ ID NO 5
<211> LENGTH: 27
<212> TYPE: DNA
<213> ORGANISM: Artificial
<220> FEATURE:
<223> OTHER INFORMATION: Forward primer for HindIII amplicon

<400> SEQUENCE: 5
aataacgttc actgtagttg gtaagct                                            27

<210> SEQ ID NO 6
<211> LENGTH: 20
<212> TYPE: DNA
<213> ORGANISM: Artificial
<220> FEATURE:
<223> OTHER INFORMATION: reverse primer for HindIII amplicon

<400> SEQUENCE: 6
aggcaatcaa gaagccagaa                                                    20

<210> SEQ ID NO 7
<211> LENGTH: 23
<212> TYPE: DNA
<213> ORGANISM: Artificial
<220> FEATURE:
<223> OTHER INFORMATION: Apcam1137 SNP forward primer

<400> SEQUENCE: 7
atgtgaacca gtctttgtgt cag                                                23

<210> SEQ ID NO 8

-continued

```
<211> LENGTH: 24
<212> TYPE: DNA
<213> ORGANISM: Artificial
<220> FEATURE:
<223> OTHER INFORMATION: Apcam1137 SNP reverse primer

<400> SEQUENCE: 8
atgctgttct tcctcagaat aacg                                          24

<210> SEQ ID NO 9
<211> LENGTH: 19
<212> TYPE: DNA
<213> ORGANISM: Artificial
<220> FEATURE:
<223> OTHER INFORMATION: Apcam1137 SNP sequencing primer

<400> SEQUENCE: 9
ggaagacgac tatgaagat                                                19

<210> SEQ ID NO 10
<211> LENGTH: 23
<212> TYPE: DNA
<213> ORGANISM: Artificial
<220> FEATURE:
<223> OTHER INFORMATION: p arm SNP forward primer

<400> SEQUENCE: 10
gtggaaacga agcatcattc tga                                           23

<210> SEQ ID NO 11
<211> LENGTH: 24
<212> TYPE: DNA
<213> ORGANISM: Artificial
<220> FEATURE:
<223> OTHER INFORMATION: p arm SNP reverse primer

<400> SEQUENCE: 11
tgctgttcta aattgcacgt ttac                                          24

<210> SEQ ID NO 12
<211> LENGTH: 17
<212> TYPE: DNA
<213> ORGANISM: Artificial
<220> FEATURE:
<223> OTHER INFORMATION: p arm SNP sequencing primer

<400> SEQUENCE: 12
cgtattgggt tgtgaga                                                  17

<210> SEQ ID NO 13
<211> LENGTH: 24
<212> TYPE: DNA
<213> ORGANISM: Artificial
<220> FEATURE:
<223> OTHER INFORMATION: q arm SNP forward primer

<400> SEQUENCE: 13
tcaaacagaa ggcagtttat tcag                                          24

<210> SEQ ID NO 14
<211> LENGTH: 23
<212> TYPE: DNA
<213> ORGANISM: Artificial
<220> FEATURE:
<223> OTHER INFORMATION: q arm SNP reverse primer

<400> SEQUENCE: 14
```

-continued gggggtaaaa taatatgccg aga                                           23

<210> SEQ ID NO 15
<211> LENGTH: 20
<212> TYPE: DNA
<213> ORGANISM: Artificial
<220> FEATURE:
<223> OTHER INFORMATION: q arm SNP sequencing primer

<400> SEQUENCE: 15
tcttagtaat gtaccagatg                                               20

<210> SEQ ID NO 16
<211> LENGTH: 8582
<212> TYPE: DNA
<213> ORGANISM: Rattus norvegicus

<400> SEQUENCE: 16
agtagtgaat tcaaaatcc tttttaacct tataggtcca agggtagcca aggatggcag      60
cagcctcata tgatcagttg ttaaagcaag ttgaggccct gaagatggag aactcaaatc    120
ttcgacaaga gctcgaagat aattccaatc accttacaga actggaaact gaggcatcta    180
acatgaagga agtacttaag cagctgcagg gaagtattga agatgagact atgacttccg    240
gacagattga tttactagag cgcccttaaag aatttaactt agatagcaat ttccccggag   300
tgaaactacg ctcgaaaatg tccctccgat cctatggaag tcgggaagga tctgtatcaa    360
gccgttcagg agaatgcagt cctgtcccca tggggtcatt cccaagaaga gcatttgtaa    420
atggaagcag agaaagcact ggatacttag aagagcttga aaagagaga tcattactcc     480 ttgctgatct tgacaaagaa gaaaaggaaa aggactggta ttatgctcag cttcagaacc    540
tcacgaaaag aatagatagc ctgcccttga ctgagaactt ttccttacag acagacatga    600
caagacggca gctggagtat gaagcacggc agatcagggc cgcaatggag gagcagcttg    660
gcacctgcca ggacatggag aaacgagcac agcgaagaat agccaggatt cagcaaatag    720
agaaggacat tcttcgtgta cggcagctct tacagtccca agcggctgaa gcagagaggt    780
catctcagag caagcatgaa actgcctccc atgaagctga gcggcagctt aaggtcaag    840 gagtggcaga aagcaacttg gcaacttctg gtagtgccca gagttcagct gcacgtgtgg    900
atcatgaaac agccggtgtt ttgagttcta gcggcacaca ctctgctcct cgaaggctga    960
cgagtcacct gggaacgaag gtggaaatgg tgtattcatt gttgtccatg cttggtactc   1020
atgataagga cgatatgtca cgaactttgc tagctatgtc tagctcccaa gacagctgta   1080
tatccatgcg acagtctgga tgtcttcctc tcctcatcca gcttttacat ggcaatgaca   1140
aagactctgt gttgttggga aattcccggg gcagtaaaga ggctcgggcc agggccagtg   1200
cagccctcca caacatcatt cactcacagc ctgatgacaa gagaggcagg cgtgaaatcc   1260
gggtccttca tcttttggaa cagatacgag cttactgcga aacctgttgg gagtggcagg   1320
aagcccatga acaaggcatg gaccaggaca aaaatccaat gccagctcct gttgagcatc   1380
agatctgccc tgcggtgtgt gttctgatga aactctcatt tgatgaggag cacagacatg   1440
cgatgaatga gcttgggggg ctgcaggcta ttgcagagtt actgcaggtg gactgtgaga   1500
tgcacgggct cactgatgac cactacagtg tcactctacg acggtacgct ggaatggcct   1560
tgacaaacct gacctttgga gatgttgcca acaaggctac gctgtgttct atgaaaggct   1620
gcatgagggc actcgtggcc cagttaaaat ccgaaagtga agacttacag caggttattg   1680

```
caagtgtttt gcggaatttg tcttggcgag cagatgtaaa tagcaaaaag acgttgagag   1740
aagttggaag tgtgaaagcg ttgatggaat gtgctttgga agttaaaaag gaatcaactc   1800
tcaaaagcgt cttgagtgcc ttatggaatc tgtccgcaca ctgcactgag aataaggctg   1860
acatatgtgc tgtggacggg gcactggcat ttctggttgg cacccctcact taccggagcc   1920 agacaaatac gttagccatc attgaaagtg gaggtgggat attacggaat gtgtccagct   1980
tgatagctac caacgaagac cacagacaaa tcctaagaga gaacaactgc ctacaaactt   2040
tattacagca cttgaaatct cacagcttga caatagtcag taatgcatgt ggaactctgt   2100
ggaatctctc agcgagaaat cctaaagacc aggaggctct gtgggacatg ggggcggtga   2160
gcatgctcaa gaacctcatt cattccaagc acaaaatgat cgctatgggg agcgcagcag   2220 cttttaaggaa tctcatggca aacagacctg caaagtataa ggatgccaac atcatgtctc   2280
ctggctcaag tttgccatcc cttcacgtta ggaaacaaaa agctctagaa gcagaattag   2340
acgctcagca tttatcagaa acctttgaca atattgacaa tttaagtccc aaggcatctc   2400
atcgcagtaa gcagagacac aagcagaatc tttatggtga ctatgtcttt gacgccagtc   2460
gacatgatga caataggtca gacaacttta acactggaaa catgactgtt ctttcaccat   2520
acttaaatac cacagtattg cccagctctt cttcatcaag gggaagttta gacagttctc   2580
gttctgagaa agacagaagt ttggagagag aacgaggtat tggcctcagc acttaccatt   2640
cagcaacaga aaatccggga acctcttcca acggggttt gcagctctct gccactgcag   2700
cccagatagc caaagtgatg gaagaagtgt ccgccctcca cacctcccag gacgacagaa   2760
gccccgcctc tgccgctgag ctccactgtg tggcggagga gaggactgca gcacgaagaa   2820
gctctgcgtc ccacacacat ccaaacacac acaacttcgc taagtcggaa agctcaaaca   2880
ggacatgctc catgccttat gccaaggtgg aatataagag atcttcaaat gacagcttaa   2940
acagtgtcac tagtagtgat ggctatggta aaggggggcca gatgaagccc tcggttgagt   3000
cctactcaga agatgatgaa ggtaagtttt gcagttatgg gcagtatcct gccgacctag   3060
cccataagat acacagtgca aatcatatgg atgataatgg tggggagctg gacacaccaa   3120
taaactacag cctcaagtac tcagatgagc agctgaactc aggaaggcag agcccctcac   3180
aaaatgaaag gtgggcaaga cccaagcatg tgatagaaga tgaaataaag caaaacgagc   3240
aaaggcaatc aagaagccag aacaccaatt ttcccgtcta ctctgagaac actgatgaca   3300
aacacctcaa gttccaacag cattttgggc aacaagagtg cgtttcccca tataggtcca   3360
ggggaaccaa tggttcagaa acaaatcgaa tgggttctag tcatgcagtt aatcaaaatg   3420
tgaaccagtc tttgtgtcag gaagacgact atgaagatga ctagcctacc aactacagtg   3480
aacgttattc tgaggaagaa cagcatgaag aagaagagag accgacaaat tacagcataa   3540
agtataatga agagaaacac catgtggatc agcctattga ttatagtcta aaatatgcca   3600
ctgacatatc ttcatcccag aagccatcat tttcattctc aaagactcca tcagtacagg   3660
gcactaaaac tgaacataac tctccaagca gtgaggctgc atctgcacct tcatctaacg   3720
ccaaaaggca gagtcagctg catccaagtt cagcacaaag aaatggtcag actccaaaag   3780
ggactgcctg caaagtcccc tccatcaacc aagagacaat gcagacttac tgtgtagaag   3840
acaccccaat atgtttctca aggtgtagtt ccttatcatc gctatcatca gctgaggatg   3900
aaataggctg tgatcagaca acacaggagg cagactctgc gaatactctg caaatagcag   3960
agataaaaga gaatgatgtg acgcggtcag ctcaagaccc tgcagtgac gtcccagccg   4020 tgtcccagag tactagaacc aagcccagca gactccaggc ttccggctta gcttcagaat   4080
```

```
ccgccaggca taaagctgtt gagttttctt caggagccaa gtctccctcc aaaagcggtg    4140
ctcagacacc caaaagtccc ccagaacact atgtccagga gacgcccctt gtattcagca    4200
ggtgtacttc tgtcagctcc ctggacagtt ttgagagtcg ctccatcgcc agctctgttc    4260
agagtgagcc atgtagtgga atggtgagtg ggattgtcag ccccagtgac cttccagaca    4320
gcccagggca gaccatgcca ccaagcagaa gcaagacccc tccccctccc cctccccac    4380 agccagtgca gaccaagaga gaggtgccaa aaactaaggt gcctgctgcc gagcagagag    4440
agggtgggcc taagcagacg gccgtgagtg cggctgtgca gagggtgcag gtcctcccgg    4500
atgccgacac tctgttacac tttgccacag agagtactcc agatgggttt tcttgttcct    4560
ctagcctaag tgctctgagt ctggatgagc cctttataca gaaagatgtg aattaagaa     4620 taatgcctcc agttcaggaa aacgacaatg ggaatgaaac tgaaccagaa cagcctgaag    4680
aatctaatga aaaccaggat aaagaggtag aaaagcctga ctctgaaaaa gacttattag    4740
atgattccga tgatgatgat attgaaatat tagaagaatg tattatttca gccatgccaa    4800
caaagtcatc acgcaaagcc aaaaagctag cccagactgc ttcaaaatta cctcctcctg    4860
tggcaaggaa accgagtcag ctgcctgtgt acaaacttct gccgtcacag agcaggctgc    4920
aggcacaaaa acatgtcagc tttacaccag gggacgatgt gccccgagtg tactgtgtgg    4980
aagggacgcc tataaacttc tccacagcaa catctctgag tgatctcaca atagaatccc    5040
ctccgaatga gctggctgct ggagatgggg ttagagcaag tgtacagtca ggtgagtttg    5100
aaaaacgaga taccattcct acagagggca gaagtacaga tgaggctcag agaggaaaag    5160
tctcctctat agctatacca gacctggatg gtagcaaagc agaggaagga gatattcttg    5220
cagaatgcat caattctgcc ctgcccaaag gaagaagcca caagcctttc gcagtgaaaa    5280
agataatgga ccaagtccaa caggcatcca tgacttcatc cggaactaac aaaaatcaaa    5340
tagacactaa gaaaaagaag cctacttcac cagtaaagcc catgccacaa atactgaat    5400 acagaactcg tgtgagaaag aatacagact caaaagttaa cgtaaatact gaagaaactt    5460
tctcagacaa taaagactca agaaacaga gcttaaaaaa caaccccaag gacttgaatg    5520
acaagctacc ggacaatgag gacagggtcc ggggaggctt actttcgat tcaccgcatc     5580 attacgcacc cattgaaggg actccttact gcttctcacg aaatgactct ttgagttctc    5640
tagattttga tgatgacgat gttgacctct ccagggaaaa ggctgagtta agaaagggca    5700
aagaaagtaa ggactccgaa gccaaagtta cctgccacac agaaccaagc tcaagccaac    5760
agtcggctag gaaggcacag gctagtacaa acatccagt gaacagaggg ccgtctaaac     5820
cactgctgca ggaacaaccc actttccccc agtcctctaa agacgtacca gacagagggg    5880
cagcaactga cgaaaaactg cagaattttg ctattgaaaa tacaccggtt tgcttttctc    5940
gaaattcttc tctgagctcc cttagtgacg ttgaccaaga aaacaacaat aacgaagaaa    6000
ctggaccagt cagagacgct gagcctgcca acgcgcaagg acagccaggc aagcctcagg    6060
catctgggta tgcgcccaag tccttcatg tggaagacac ccctgtgtgc ttctccagaa     6120
acagctctct cagctctctg agcattgatt ctgaggacga cctgttgcga gagtgcataa    6180
gctctgctat gccaaaaaag aggaggcctt ccagactcaa gggtgaggt gagtggcaga     6240 gtcctaggaa agtgggcagc gtgttagccg aagatctgac actcgacttg aaagatatac    6300
agaggccaga gtcagaacac ggtttatccc ccgattcaga aatttcgac tggaaagcta     6360 ttcaggaagg tgcaaactcc atagtaagta gtctgcacca agctgccgcc gccgccgcgt    6420
```

| | |
|---|---|
| gtctgtccag acaagcgtcg tcggactcag actccatcct gtccctgaag tcgggcgtct | 6480 |
| ccctggggtc gccttttcac cttacacctg accaagagga gaagccattc acaagtcata | 6540 |
| aaggcccaag aattctcaaa cctggggaga aaagcacatt agaagcaaaa aaaatagaat | 6600 |
| ccgaaaacaa aggaatcaaa ggtggaaaaa aggtttataa aagcttgatt acaggaaaga | 6660 |
| ttcgatctaa ttcagaaatc tccagccaaa tgaaacaacc ccttcagaca acatgccttt | 6720 |
| caatctcaag aggcaggaca atgattcaca tcccgggagt tcggaacagc tcctcaagta | 6780 |
| caagccctgt ctctaaaaaa ggcccacccc tcaagactcc agcctctaaa gccccagtg | 6840 |
| aaggtcctgt agctaccact tctcctcgtg aactaagcc agcagtgaag tcagagctga | 6900 |
| gccctattac caggcaaact tcccacatta gtgggtcaaa taaggggccc tctaggtcag | 6960 |
| ggtctagaga ctccactccc tcgagaccca cacagcagcc attaagtagg ccgatgcagt | 7020 |
| cgccagggcg gaactcgatc tcccccggta gaaatggaat aagcactcct aacaaactct | 7080 |
| ctcagctgcc cagaacatcg tctcccagta ctgcttcgac caagtcctcg ggtcgggga | 7140 |
| aaatgtccta cacatcccca ggccggcagc tgagccagca aaacctcagc aaacaaacag | 7200 |
| gcttgtccaa gaacgccagc agcatcccca gaagtgagtc agcatccaaa ggactgaatc | 7260 |
| agatgaataa cagcaatggg tctaataaaa aggtagaact ttctagaatg tcttcaacta | 7320 |
| agtcaagtgg aagtgaatca gacaggtcag aaagacctgc attagtacgc cagtccactt | 7380 |
| tcatcaaaga agccccaagc ccaaccctaa ggaggaaact ggaggaatct gcctcatttg | 7440 |
| aatcccttc tccatcttct agaccagatt ctcccaccag gtcccaggca cagaccccag | 7500 |
| ttttaagccc ttcccttccc gatatgtctc tgtccacaca tccatctgtt caggcaggtg | 7560 |
| gatggcgcaa gctcccacct aacctcagcc ccactataga gtacagtgac ggaaggccct | 7620 |
| caaagcggca tgatatcgca cgctcccatt ctgaaagtcc gtccagacta ccagtcaacc | 7680 |
| gagcgggaac ctggaagcgt gaacacagca acattcctc atcccttcct cgagtgagca | 7740 |
| cttggagaag aactggaagc tcatcttcta ttctttctgc ttcttcagag tccagtgaaa | 7800 |
| aagcaaaaag tgaggatgaa aagcatgtga actctgtgcc aggacccaga caaatgaaag | 7860 |
| aaaaccaggt acccacaaaa ggaacatgga ggaaaataaa ggaaagtgaa atttctccca | 7920 |
| caaacacggt ttctcagacc acttcctcag gtgctgccag tggtgctgaa tcaaagactc | 7980 |
| tgatctatca gatggcacct gctgtttcta gaacagagga cgtttgggtg agaattgagg | 8040 |
| actgccccat taacaaccct agatctggaa gatctcccac aggtaacacc cccccagtga | 8100 |
| ttgacagcat ttcagaaaag ggaaatccaa gcattaaaga ttcaaaagac acccaaggaa | 8160 |
| aacaaagtgt gggcagtggc agtcctgtgc aaaccgtggg tctagaaaac cgcctgaact | 8220 |
| cctttattca ggtagaggcc ccggaacaga aggaactga gactaaagca ggacagggta | 8280 |
| gccctgcccc tgtagcagag actggtgaga cctgcatggc agagcgcacc cctttcagtt | 8340 |
| caagtagctc cagcaagcac agttctccca gtgggacggc cgctgccaga gtgacgcctt | 8400 |
| ttaattacaa cccaagccct aggaaaagca gcgcagacag cacttcagcc cggccatctc | 8460 |
| agatccccac tccggtgggc agcagcacaa agaagagaga ctcgaagact gacagcactg | 8520 |
| aatctagtgg agcccagagt cctaaacgcc attctgggtc ttacctcgtg acgtctgttt | 8580 |
| aa | 8582 |

<210> SEQ ID NO 17
<211> LENGTH: 50
<212> TYPE: PRT
<213> ORGANISM: Human

-continued

```
<400> SEQUENCE: 17

Arg Val Gly Ser Asn His Gly Ile Asn Gln Asn Val Ser Gln Ser Leu
1               5                   10                  15

Cys Gln Glu Asp Asp Tyr Glu Asp Lys Pro Thr Asn Tyr Ser Glu
            20                  25                  30

Arg Tyr Ser Glu Glu Glu Gln His Glu Glu Glu Glu Arg Pro Thr Asn
        35                  40                  45

Tyr Ser
    50

<210> SEQ ID NO 18
<211> LENGTH: 50
<212> TYPE: PRT
<213> ORGANISM: Dog

<400> SEQUENCE: 18

Arg Val Gly Ser Asn His Gly Ile Asn Gln Asn Val Asn Gln Ser Leu
1               5                   10                  15

Cys Gln Glu Asp Asp Tyr Glu Asp Lys Pro Thr Asn Tyr Ser Glu
            20                  25                  30

Arg Tyr Ser Glu Glu Glu Gln His Glu Glu Glu Glu Arg Pro Thr Asn
        35                  40                  45

Tyr Ser
    50

<210> SEQ ID NO 19
<211> LENGTH: 50
<212> TYPE: PRT
<213> ORGANISM: Cow

<400> SEQUENCE: 19

Arg Val Gly Ser Asn His Gly Ile Ser Gln Asn Val Asn Gln Ser Leu
1               5                   10                  15

Cys Gln Glu Asp Asp Tyr Glu Asp Lys Pro Thr Asn Tyr Ser Glu
            20                  25                  30

Arg Tyr Ser Glu Glu Gly Gln His Glu Glu Glu Glu Arg Pro Thr Asn
        35                  40                  45

Tyr Ser
    50

<210> SEQ ID NO 20
<211> LENGTH: 50
<212> TYPE: PRT
<213> ORGANISM: Rat

<400> SEQUENCE: 20

Arg Met Gly Ser Ser His Ala Val Asn Gln Asn Val Asn Gln Ser Leu
1               5                   10                  15

Cys Gln Glu Asp Asp Tyr Glu Asp Lys Pro Thr Asn Tyr Ser Glu
            20                  25                  30

Arg Tyr Ser Glu Glu Glu Gln His Glu Glu Glu Glu Arg Pro Thr Asn
        35                  40                  45

Tyr Ser
    50

<210> SEQ ID NO 21
<211> LENGTH: 51
<212> TYPE: PRT
```

```
<213> ORGANISM: Mouse

<400> SEQUENCE: 21

Arg Met Gly Ser Ser His Ala Ile Asn Gln Asn Val Asn Gln Ser Leu
1               5                   10                  15

Cys Gln Glu Asp Asp Tyr Glu Asp Asp Lys Pro Thr Asn Tyr Ser Glu
            20                  25                  30

Arg Tyr Ser Glu Glu Glu Gln His Glu Glu Glu Glu Arg Pro Thr
        35                  40                  45

Asn Tyr Ser
    50

<210> SEQ ID NO 22
<211> LENGTH: 50
<212> TYPE: PRT
<213> ORGANISM: Opossum

<400> SEQUENCE: 22

Arg Val Ser Ser Gly His Gly Ile Asn Gln Lys Val Asn Gln Ser Leu
1               5                   10                  15

Cys His Glu Asp Asp Tyr Asp Glu Asp Lys Pro Thr Asn Tyr Ser Glu
            20                  25                  30

Arg Tyr Ser Glu Glu Glu Gln His Glu Glu Glu Asp Arg Pro Thr Asn
        35                  40                  45

Tyr Ser
    50

<210> SEQ ID NO 23
<211> LENGTH: 48
<212> TYPE: PRT
<213> ORGANISM: Zebrafish

<400> SEQUENCE: 23

Ser Ser Gly Ser Ser His Gly Leu Asn Lys Lys Ile Ser Gln Thr Ile
1               5                   10                  15

Cys Ser Val Asp Asp Tyr Ala Asp Asp Lys Pro Thr Asn Tyr Ser Glu
            20                  25                  30

Arg Tyr Ser Glu Glu Glu Gln Leu Glu Glu Gln Thr Pro Ser Tyr Ser
        35                  40                  45
```